(12) United States Patent
Yaroslavsky et al.

(10) Patent No.: US 11,627,908 B2
(45) Date of Patent: Apr. 18, 2023

(54) INSTRUMENTS AND METHODS FOR IMAGING COLLAGEN STRUCTURE IN VIVO

(71) Applicants: THE UNIVERSITY OF MASSACHUSETTS, Boston, MA (US); THE GENERAL HOSPITAL CORPORATION, Boston, MA (US)

(72) Inventors: Anna N. Yaroslavsky, North Andover, MA (US); Victor Neel, Boston, MA (US)

(73) Assignee: UNIVERSITY OF MASSACHUSETTS, Boston, MA (US)

( * ) Notice: Subject to any disclaimer, the term of this patent is extended or adjusted under 35 U.S.C. 154(b) by 572 days.

(21) Appl. No.: 16/499,736

(22) PCT Filed: Mar. 30, 2018

(86) PCT No.: PCT/US2018/025487
§ 371 (c)(1),
(2) Date: Sep. 30, 2019

(87) PCT Pub. No.: WO2018/183905
PCT Pub. Date: Oct. 4, 2018

(65) Prior Publication Data
US 2021/0052212 A1   Feb. 25, 2021

Related U.S. Application Data

(60) Provisional application No. 62/479,749, filed on Mar. 31, 2017.

(51) Int. Cl.
*A61B 5/00* (2006.01)
*A61B 90/00* (2016.01)
(Continued)

(52) U.S. Cl.
CPC ............ *A61B 5/441* (2013.01); *A61B 5/0064* (2013.01); *A61B 5/0082* (2013.01); *A61B 90/39* (2016.02);
(Continued)

(58) Field of Classification Search
CPC ..... A61B 5/441; A61B 5/0064; A61B 5/0082; A61B 90/39; A61B 2090/3904;
(Continued)

(56) References Cited

U.S. PATENT DOCUMENTS 7,289,211 B1 * 10/2007 Walsh, Jr. ................ G01J 4/04
356/369
2004/0133112 A1   7/2004 Rajadhyaksha
(Continued)

FOREIGN PATENT DOCUMENTS

WO        2014165820 A1   10/2014

OTHER PUBLICATIONS

Wang et al. "Systematic Design of a Cross-Polarized Dermoscope for Visual Inspection and Digital Imaging." IEEE Instrumentation & Measurement Magazine, Dec. 2011, pp. 26-31 (Year: 2011).*
(Continued)

*Primary Examiner* — Jon Chang
(74) *Attorney, Agent, or Firm* — Brake Hughes Bellermann LLP

(57) ABSTRACT

Instruments and methods for wide-field polarized imaging of the skin to determine an outer lesion margin objectively in vivo to provide guidance to a surgeon. Quantitative characterization of collagen structures in the skin can be used to determine the outer lesion margin or monitor skin treatment.

25 Claims, 33 Drawing Sheets

(51) Int. Cl.
*G06T 7/136* (2017.01)
*G06T 7/00* (2017.01)
*G16H 30/40* (2018.01)

(52) U.S. Cl.
CPC ............ *G06T 7/0016* (2013.01); *G06T 7/136* (2017.01); *G16H 30/40* (2018.01); *A61B 2090/3904* (2016.02); *G06T 2207/30088* (2013.01); *G06T 2207/30096* (2013.01)

(58) Field of Classification Search
CPC ... A61B 2576/02; A61B 5/444; A61B 5/0068; A61B 5/0071; A61B 5/0066; A61B 5/0077; A61B 5/443; A61B 5/4836; A61B 5/742; A61B 5/7207; A61B 5/6835; G06T 7/0016; G06T 7/136; G06T 2207/30088; G06T 2207/30096; G16H 30/40; G01N 21/21
See application file for complete search history.

(56) References Cited

U.S. PATENT DOCUMENTS

| | | |
|---|---|---|
| 2005/0094147 A1* | 5/2005 | Yaroslavsky ........ A61B 5/0059 356/417 |
| 2013/0324846 A1 | 12/2013 | Yaroslavsky et al. |
| 2015/0164327 A1 | 6/2015 | Yaroslavsky et al. |
| 2015/0374276 A1* | 12/2015 | Farkas ................... A61B 5/443 600/407 |
| 2016/0066833 A1 | 3/2016 | Yaroslavsky et al. |

OTHER PUBLICATIONS

International Search Report and Written Opinion from PCT Application No. PCT/US2018/025487, dated Jun. 15, 2018, 8 pages.
Yaroslavsky, Anna N, et al., "Optical mapping of nonmelanoma skin Cancers—A pilot clinical study", Lasers in Surgery and Medicine, vol. 49, May 23, 2017, pp. 803-809.
Communication pursuant to Rule 164(1) EPC for European Application No. 18776460.0, dated Dec. 22, 2020, 15 pages.

* cited by examiner

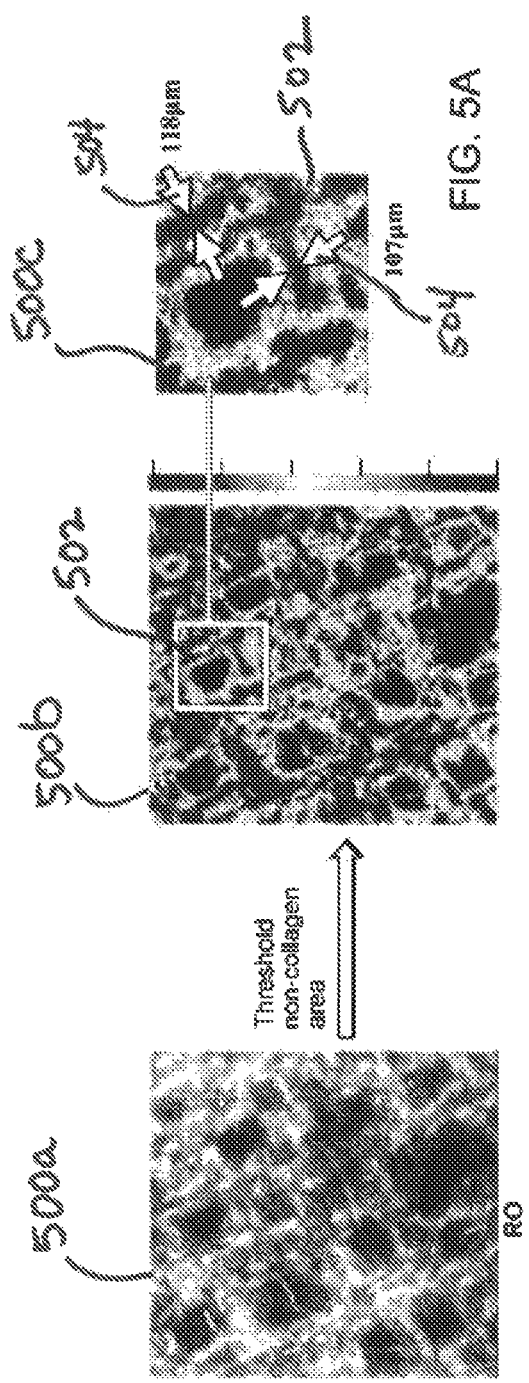

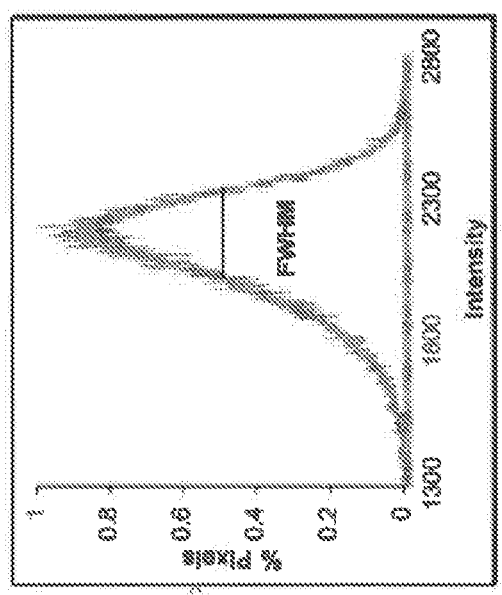
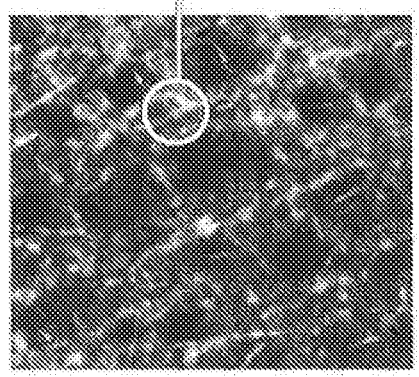
FIG. 5B

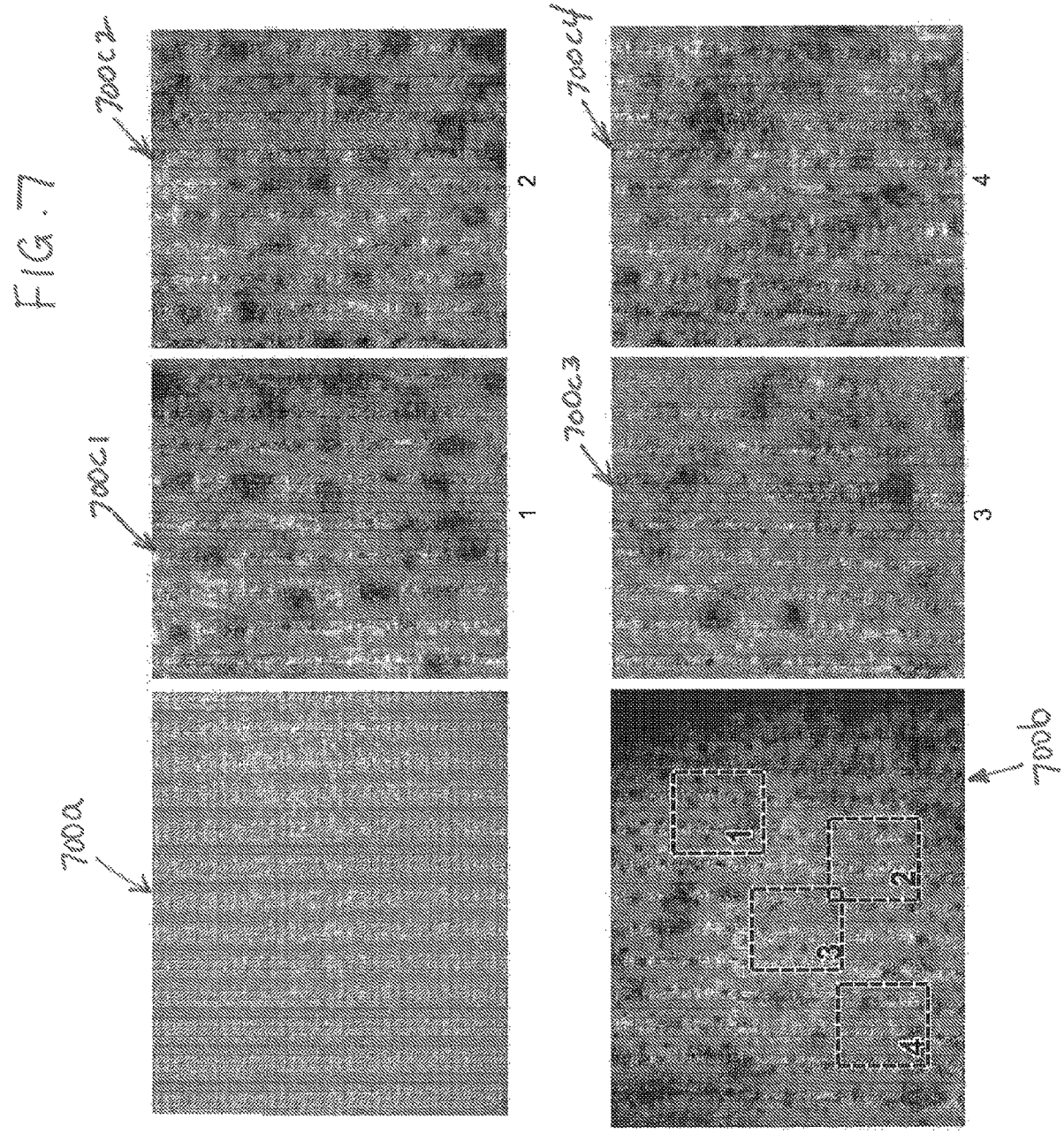

25 year old subject 35 year old subject 65 year old subject

Young
Immunohistochemical Type III collagen

Senior

Young
Second Harmonic Generation

Senior

Young
This Study

Senior co-polarized image cross-polarized image (dermis)

Subtraction: *Co-pol – Cross-pol* polarization image (epidermis)

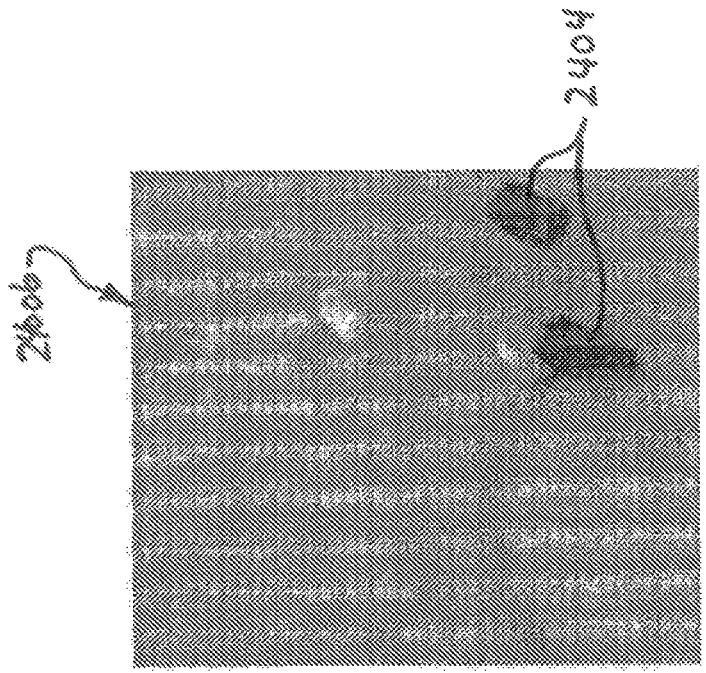
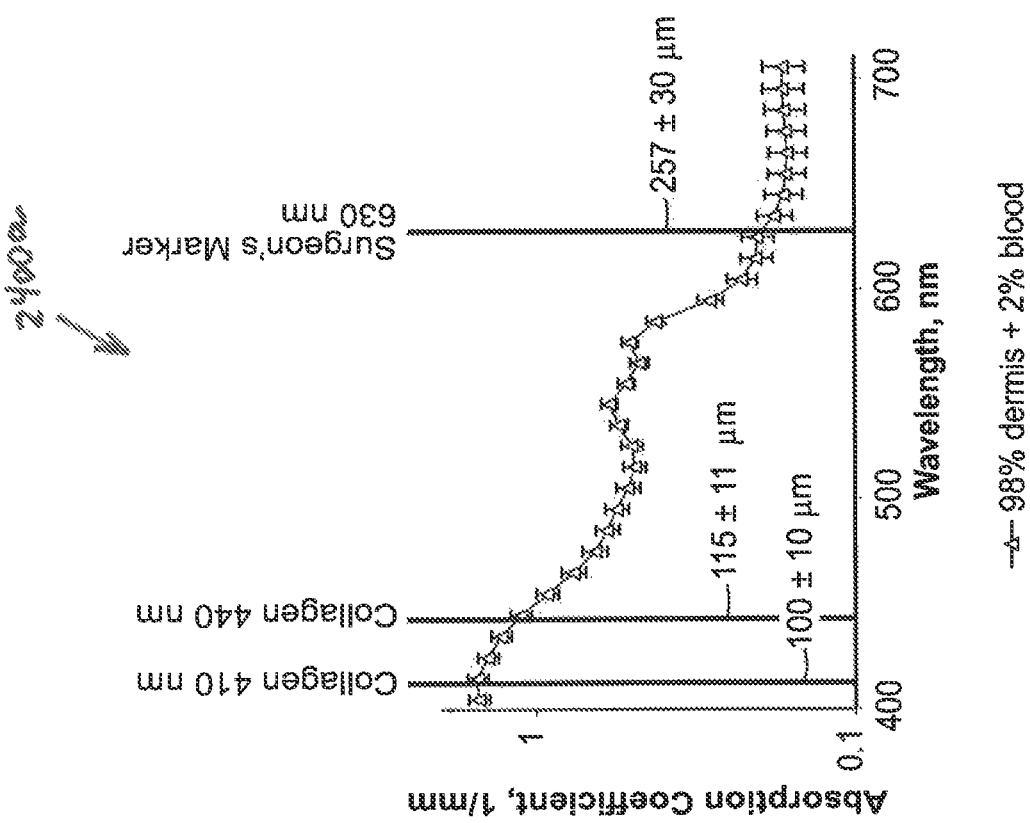
FIG. 24B
FIG. 24A 630 nm Surgeon's Marker 440 nm Collagen Image 410 nm Collagen Image

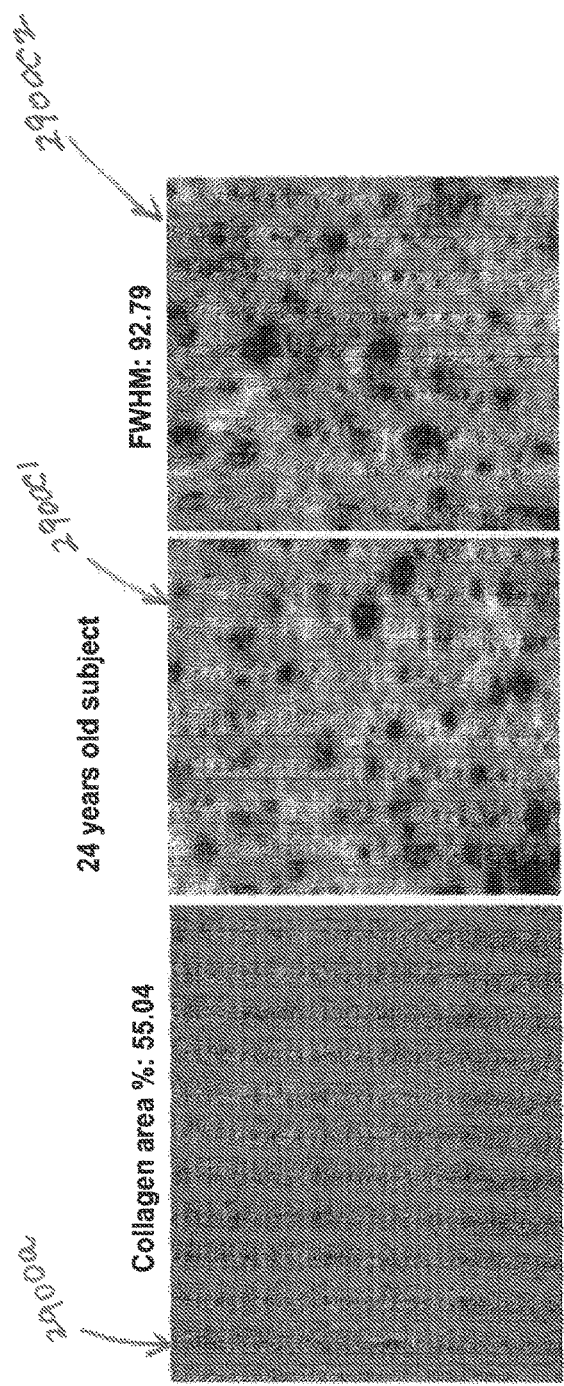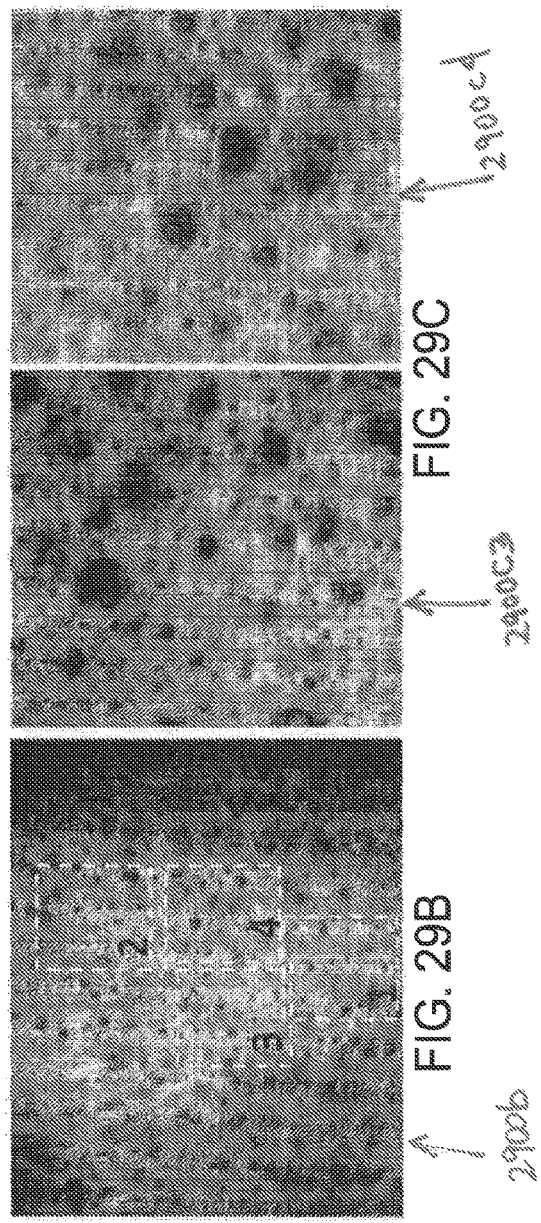
FIG. 29A
FIG. 29B
FIG. 29C

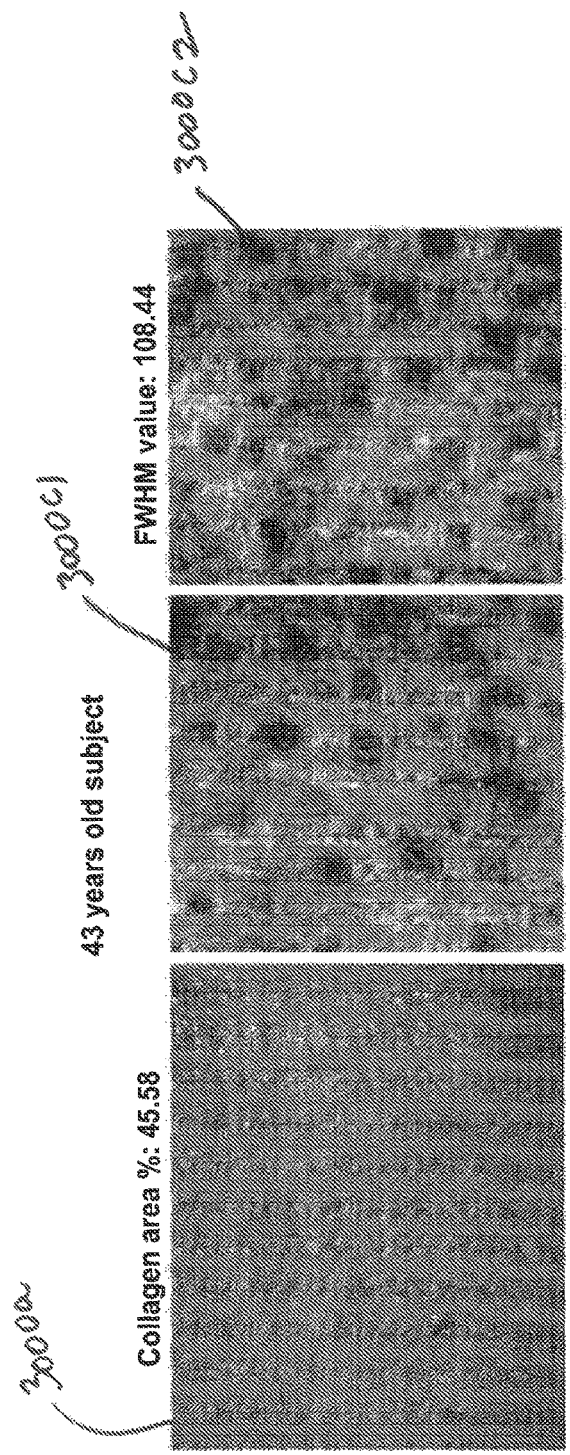
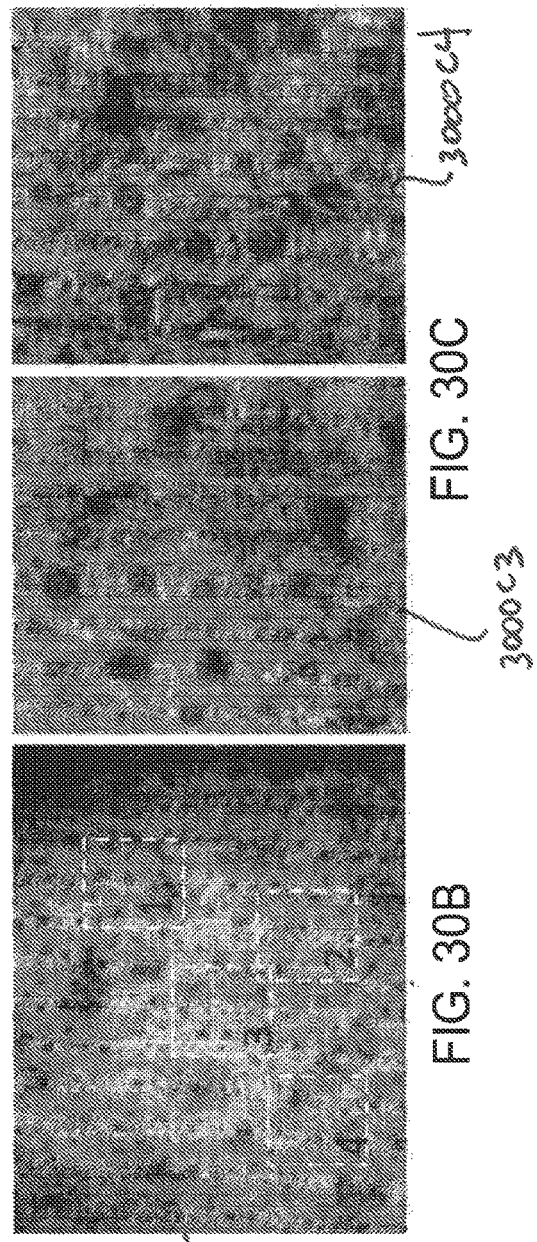
FIG. 30A
FIG. 30B
FIG. 30C

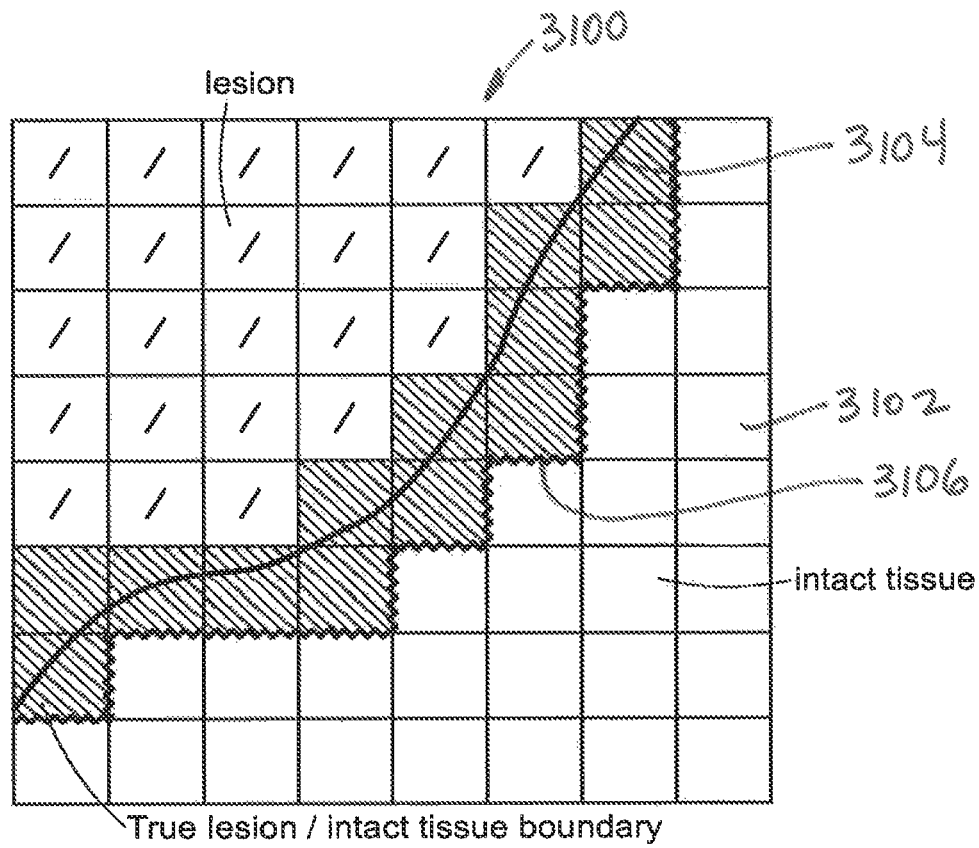
 – Subareas characterized as "borderline"
∿∿∿ – Accepted "outer" lesion margin
FIG. 31

INSTRUMENTS AND METHODS FOR IMAGING COLLAGEN STRUCTURE IN VIVO

CROSS REFERENCE TO RELATED APPLICATION(S)

This application is a 35 U.S.C. § 371 National Phase Entry Application from PCT/US2018/025487 filed Mar. 30, 2018, designating the United States and claiming priority to U.S. Application 62/479,749, filed Mar. 31, 2017, the disclosures of which are incorporated by reference herein in their entireties.

FIELD OF THE INVENTION

The subject disclosure relates to instruments and methods for using Optical Polarization Imaging (OPI) prior to surgery to detect the extent of subclinical tumor spread by monitoring disruption in collagen.

BACKGROUND OF THE RELATED ART

Skin is the first layer of protection for the human body against outside environment. Skin diseases and degeneration can be related to sun exposure, working environment and personal habits, which can be observed in the change of internal structure of skin. Collagen, which is the major component of the dermal structure, is an important factor related to dermal changes. Thus, it is beneficial to inspect collagen structure and quantitatively define the status of skin. Histopathological and immunohistochemical studies are commonly used for diagnosing diseases and evaluating dermal changes. These techniques require biopsy, which may cause discomfort, scarring and infection and cannot be performed either in vivo or in real time.

Several imaging techniques such as two photon microscopy, second harmonic generation and reflectance confocal microscopy are also used to interpret skin structure. Confocal microscopy is an imaging method with cellular resolution but due to the shallow imaging depths, this approach does not yield high contrast, high resolution images of collagen structure in vivo. Non-linear microscopy techniques such as two photon microscopy and second harmonic generation offer high-resolution morphological detail and deeper light penetration depth, but thus far it has not shown potential for in vivo visualization of dermal structure, due to high power densities required for imaging and the very small field of view.

Nonmelanoma skin cancers (NMSCs), including basal cell carcinoma and squamous cell carcinoma, are the most common malignancy in the United States. Surgery is the most common treatment for these tumors, but pre-operative identification of surgical margins is challenging.

Mohs micrographic surgery (MMS) is the mainstay of treatment for high-risk NMSCs. In routine MMS, the Mohs surgeon begins by making a clinical assessment of the tumor boundary often solely relying on visual markers such as erythema, scale, or texture of the lesion. Typically, the surgeon draws a surgeon's marker right on the patient's skin with a purple pen. The surgeon then proceeds to remove the tissue that clinically appears abnormal with an additional margin of 1-2 mm of normal-appearing skin. The aim of the surgery is to maximize preservation of normal skin while removing the tumor in its entirety. The excised tissue is then oriented, marked, and processed via intraoperative horizontal frozen sections to assess the presence (i.e., positive margin) or absence (i.e., negative margin) of malignant cells at the surgical margin. The advantage of MMS compared to conventional resection surgery is that it allows complete analysis of the entire margin. If lateral and deep margins are found to be clear of malignant cells, the surgeon proceeds to repair the defect. However, if cancer cells are detected at the margins, additional tissue is removed and the steps are repeated until clear margins are obtained.

NMSCs necessitating MMS most often involve the patient's face and frequently require more than one stage for complete histopathological clearance. Mohs surgeons find identifying adequate surgical margins presurgically to be challenging because of the lack of information from simple visual inspection. Typically, more than one stage for tumor clearance is required. Some surgeons do a better job than others. This is not only inefficient and erratic but prolongs the duration and extent of the Mohs procedure and adds substantial cost.

One challenge leading to the need for multiple surgical stages during MMS is the difficulty of clinically identifying the boundaries of the tumor prior to surgery. Normal-appearing skin can often harbor tumor and conversely, inflamed or atypically-pigmented tissue can arouse suspicion in the surgeon but be tumor-free on microscopic analysis.

Histopathological and immunohistochemical studies are commonly used for diagnosing diseases and evaluating dermal changes. These techniques require biopsy, which may cause scarring and infection and cannot be performed either in vivo or in real time. Several imaging techniques such as two photon microscopy, second harmonic generation and reflectance confocal microscopy are also used to visualize skin structure. Confocal microscopy is a mature imaging technique with submicron cellular resolution but has inadequate imaging depths, so collagen structure is not visualized in vivo. Non-linear microscopy techniques, such as two photon microscopy and second harmonic generation, offer high-resolution morphological detail and deeper light penetration depth and have overcome some of the limitations of confocal microscopy. But due to a requirement for higher power densities needed to achieve good quality images and a very small field of view, this imaging method is also not suitable for in vivo analysis of deeper dermal collagen structure.

SUMMARY

In view of the above, a continuing need exists for improvements for in vivo imaging of the skin and skin related tumors. A non-invasive and simple-to-use technology to improve the surgeon's estimation of the tumor margins preoperatively reduces variability in the total number of surgical stages per case and in streamlining the overall procedure. A variety of imaging tools have been examined in the past to aid detection of cutaneous pathology, including reflectance confocal microscopy (RCM), optical coherence tomography (OCT), Raman spectroscopy, and second harmonic generation. While each device has certain advantages, shortfalls limit their use in the clinical setting for Mohs surgery. For instance, reflectance confocal microscopy provides high resolution imaging at superficial depths up to 200 μm limiting the application in imaging lesions extending into the dermis. Furthermore, technical barriers such as artifact formation due to patient motion and the slow pace of imaging can be limiting factors.

Optical coherence tomography provides deeper penetration but suffers from inaccuracy and unreliable differentiation between lesions such as basal cell carcinomas and actinic keratoses. Raman spectroscopy is time consuming, requiring up to 60 minutes for diagnosis. And second harmonic generation provides high resolution images but at the cost of a limited field of view. While both RCM and OCT devices are available commercially to Mohs surgeons, neither has been widely adopted.

The subject technology provides a safe and efficient imaging alternative of optical polarization imaging (OPI) to image skin and specifically dermal collagen to aid surgeon's in determining proper marking in vivo. Visible light at 440 nm is used for illumination and cross-polarization imaging to allow for rapid, noninvasive quantitative assessment of dermal collagen structure. This approach has a resolution of approximately 12 microns. Alteration in collagen composition, in particular due to collagenases secreted by tumors, is apparent in the images. Such changes in this otherwise uniform dermal lattice serve as a marker or guide for the presence of malignancy. Tumor-induced disruption in the collagen network is visualized and evaluated for delineating the affected tissue boundaries prior to Mohs surgery. Ultimately, by visualizing the tumor boundaries accurately in vivo prior to the first surgical excision, the patient and the surgeon benefit.

The present technology also relates to the instruments and methods to perform OPI. In one embodiment, the instrument is a polarization-sensitive, wide-field, reflectance imaging instrument to image collagen structure and measure changes in dermal conditions. Preferred embodiments provide an in vivo rapid assessment of large skin areas with optical sectioning capability. An imaging detector and light source are positioned to illuminate the surface of a region of skin with one or more wavelengths of light. Polarized images are obtained at the tissue surface and at different selected depths beneath the dermal surface. In a preferred embodiment, the detector is spaced at a selected distance from an optical surface that can contact the surface of the skin to be imaged. A calibration reference can be used to enable quantification of characteristics of the tissue from the detected images.

A preferred embodiment can employ the imaging methods described herein to pre-operatively determine a margin around tissue to be treated or removed during a surgical procedure. During Mohs surgery, for example, surgeons rely upon purely visual determination of the tumor boundary to define the margin. Often there is tissue residing outside of the margin that should also be removed that is only determined after one or more histological examinations of the removed sample. Using the procedures described herein, more accurate boundaries can be identified in advance, thereby substantially reducing the time for the procedure and preventing the need for subsequent procedures.

A preferred embodiment can utilize a hand-carried instrument in which the imaging detector and light source can be housed for portability and ease of use. An imaging aperture can be spaced at a fixed distance from a polarizing element to select a co-polarized or cross-polarized image and a lens that optically couples the image at the aperture onto the light receiving surface of the detector. The imaging aperture can be an optically transmissive element such as a glass window that can contact the skin. The entire aperture can be illuminated simultaneously to provide uniform illumination of the region of the skin being imaged in a single shot at each of a plurality of wavelengths.

In one embodiment, the subject technology is directed to an instrument for imaging a region of tissue to optimize in vivo determination of a boundary of a tumor including an illuminator for illuminating the region with at least one wavelength of light. An imaging detector generates images of the region based upon cross-polarized light reflected from the region, wherein the at least one wavelength determines a depth of the images in the tissue. A controller connects to the imaging detector for receiving and storing the images, wherein the depth of the images in the tissue is selected to illustrate a collagen structure of the tissue so that the images are presented to a surgeon for determining surgical margins around the tumor based upon disruption in the collagen structure. Preferably, the at least one wavelength is adjusted to match a depth of the collagen structure according to a location of the region on the patient. The at least one wavelength can be in a range of 350 nm to 750 nm and, more preferably is in the range of 380 nm to 550 nm. Most preferably, the range is 400 nm to 480 nm with FWHM of up to 20 nm. The instrument also functions without use of a contrast agent. The instrument may use light that is monochromatic, typically blue.

The instrument may further include a treatment device coupled to the controller for removing a portion of the region according to the surgical margins. The controller may direct the treatment device, such as an ablation laser, to remove the tissue within the surgical margins. The boundary of the tumor is accurately seen because, for example, the presence of basal cell carcinoma causes the disruption of the collagen structure which results in a localized darkening in the images. The images are taken in vivo with an initial surgeon's marker drawn on the tissue. Hence, the surgeon can review his initial surgeon marker and make adjustments as needed based upon the additional insight seen in the images. In effect, the initial surgeon's marker maps the image on to the patient. As necessary, the images can be retaken once the surgeon marker is redrawn to again verify accuracy and repeated as deemed appropriate.

The instrument may superimpose the boundary delineating the tumor based on analysis of the images upon at least one of the images. The boundary may be determined based upon the plurality of images. For example, sub-areas of the images may be classified based upon reflectance as showing the tumor, normal tissue and transitional between the two. As such, once the transitional areas are identified, these areas can be marked as such on the image. In another embodiment, a line can be best fit through the transitional areas to represent the tumor or increased by a predetermined amount to illustrate a proposed surgeon marker. In an alternative embodiment, the outward or normal side edge of the transitional areas can be used as an outer lesion marker.

Typically, the controller determines the surgical margins by: comparing a reflectance value of each of the images to a normal reflectance value, wherein: when the reflectance value of the images is below the normal reflectance by a predetermined amount, an area associated with the respective image is identified as an unhealthy area; and when the reflectance value of the images is within the predetermined amount of the normal reflectance, an area associated with the respective image is identified as a healthy area; and forming the surgical margins based upon transitions from the unhealthy areas to the healthy areas. For calibration, the instrument can collect normal images from a healthy region of tissue and determine the normal reflectance value based upon the normal images. The reflectance value can also be fairly standard based upon factors selected from the group consisting of: an age of the patient; a location of the region; quantified parameters of pixel intensity distribution; collagen-occupied area defined as a percentage of pixels above a certain threshold brightness; and a quantitative measure of the degree of order in the image, such as approximate entropy or Tsallis entropy; and combinations thereof. In any application, the controller can apply thresholding to the images for increased contrast.

Preferably, the controller is further operative to: form a number of sub-areas of the images; classify each sub-area as one of: lesion; normal; and borderline based upon a reflectance of the sub-area, wherein: borderline is reflectance within a range; normal is reflectance above the range; and lesion is reflectance below the range; and form an outer margin from stitching together consecutive borderline sub-areas. This information may be superimposed upon an image with an initial surgeon's marker to map the outer margin on to the patient. Alternatively, various markings may be employed on the patient to allow mapping the outer margin as determined by the controller. Since the images are in vivo, the patient may be held steady during the controller analysis and a marker controlled by the controller may draw the calculated outer margin on to the patient. Again, the process may be repeated with such marking for further evaluation and review by the surgeon.

In another embodiment, the subject technology is an instrument for imaging a region of tissue to evaluate collagen structure comprising: an illumination ring for illuminating the region with at least one wavelength of light; an imaging detector for generating images of the region based upon cross-polarized light reflected from the region over a period of time; and a controller connected to the imaging detector for receiving and storing the images, wherein the images are of a depth in the tissue that illustrates the collagen structure so that the images are compared over the period of time to evaluate a treatment of the region.

It should be appreciated that the subject technology can be implemented and utilized in numerous ways, including without limitation as a process, an apparatus, a system, an instrument, a method for applications now known and later developed and a computer readable medium. These and other unique features of the technology disclosed herein will become more readily apparent from the following description and the accompanying drawings.

BRIEF DESCRIPTION OF THE DRAWINGS

So that those having ordinary skill in the art to which the disclosed technology appertains will more readily understand how to make and use the same, reference may be had to the drawings.

FIGS. 5A and 5B illustrate series of images that are processed to generate quantitative data in accordance with preferred embodiments of the subject disclosure.

FIG. 7 shows a series of images for a subject including a digital picture of the skin, a 410 nm cross-polarization image; and four indicated regions of interests, respectively.

FIG. 24A is a graph of absorption coefficient against wavelength in accordance with the subject technology.

FIGS. 24B-24E are images obtained at different wavelengths in accordance with the subject technology.

FIGS. 29A-29C are a series of images of the skin of a patient at a younger age.

FIGS. 30A-30C are a series of images of the skin of a patient at an older age.

FIG. 31 shows an example of a computed margin in accordance with the subject disclosure.

DETAILED DESCRIPTION OF THE INVENTION

Figure 1A:
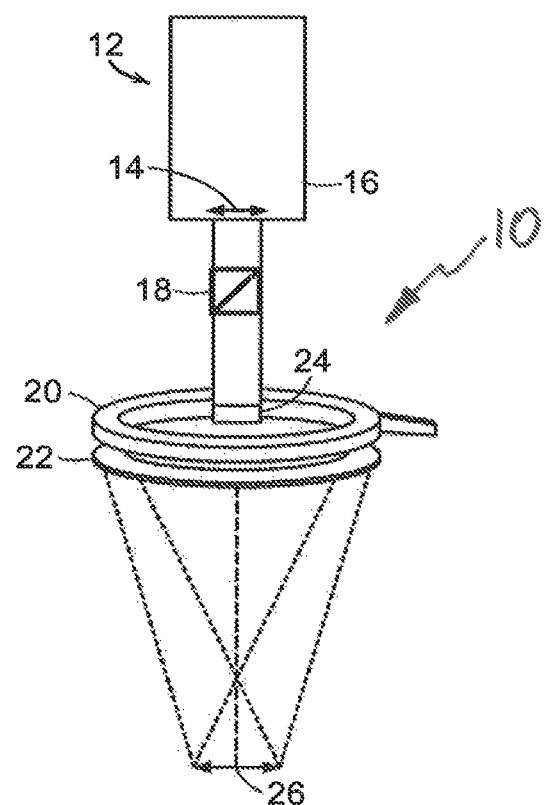
FIGS. 1A and 1B show schematic illustrations of a wide-field imaging instrument in accordance with preferred embodiments of the subject disclosure.

The subject technology overcomes many of the prior art problems associated with in vivo examination of skin. The advantages, and other features of the instruments and methods disclosed herein, will become more readily apparent to those having ordinary skill in the art from the following detailed description of certain preferred embodiments taken in conjunction with the drawings which set forth representative embodiments of the present invention and wherein like reference numerals identify similar structural elements.

Figure 1B:
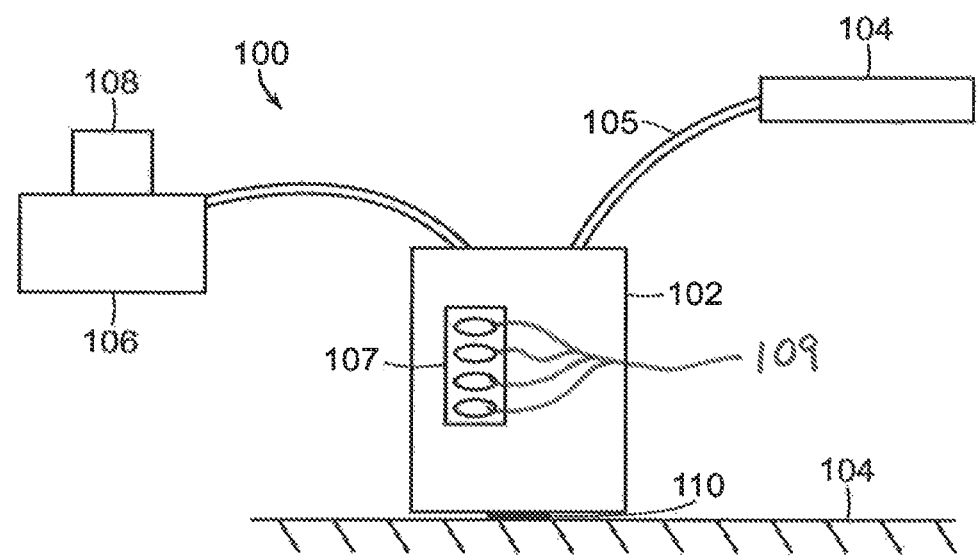

Referring now to FIG. 1A, a schematic view of the light delivery and detector elements 10 of a wide-field imaging instrument 100 (FIG. 1B) is shown. The instrument 100 can generate images of collagen structures of the skin with intact epidermis. FIG. 1B shows a schematic view of the instrument 100 including a handheld unit 102. As shown in FIG. 1A, the light delivery and detector elements 10 include a camera housing 12 in which a detector 16 such as CCD or CMOS camera is positioned to receive a cross-polarized image 14 from polarizing beamsplitter 18 and a lens 24. Illumination is provided by an LED ring 20, for example, that delivers polarized light using a linear polarizer 22, onto a field of view 26 on a tissue surface. The elements 10 can be integrated, as shown in FIG. 1B, into a handheld unit 102 of a portable diagnostic imaging instrument 100.

The handheld unit 102 can either include the light source such as the LED illumination of FIG. 1A, and/or can be connected to an external light source 104 with a fiber optic cable 105 as shown in FIG. 1B. The detector 16 in housing 12 (FIG. 1A) of the handheld unit 102 collects images from an aperture 110 for sending image data over cable or wireless connection to a data processor such as a computer 106 having a memory for storing images. Images and data can be displayed on an electronic display 108 or sent via wireless or wired connection over a network such as the Internet. The handheld unit 102 can include the illuminator, lens, polarizers, window aperture 110, as well as all the elements of FIG. 1A as described herein, and can be battery operated. An internal data processor and power regulator can also be included in the handheld unit 102 along with a control panel 107 having buttons 109 to control instrument operations.

In a preferred embodiment, a filtered lamp such as xenon or mercury arc lamp, or a halogen or metal halide light source can be combined with four narrow bandpass filters (full width at half maximum up to 20 nm, center wavelengths of 410 nm, 440 nm, 570 nm and 650 nm). In another embodiment, the filtered lamp can be combined with three narrow bandpass filters (full width at half maximum up to 20 nm, center wavelengths of 440 nm, 570 nm, and 650 nm). The filtered light is delivered with fiber optic cable configured into an annular array at a distal end to provide the illumination. An array of lasers, such as laser diodes, can also be used. Light is preferably delivered to the skin via a fiber-optic linearly polarizing ring-light illuminator with appropriate power density. Cross-polarized images can be acquired using a CCD camera coupled with an objective lens (0.5× lens) and linearly polarizing filter. The linearly polarizing filter is in the pathway of incident light and a polarizing beam splitter is in the pathway of light collected by the camera.

Figure 2A:
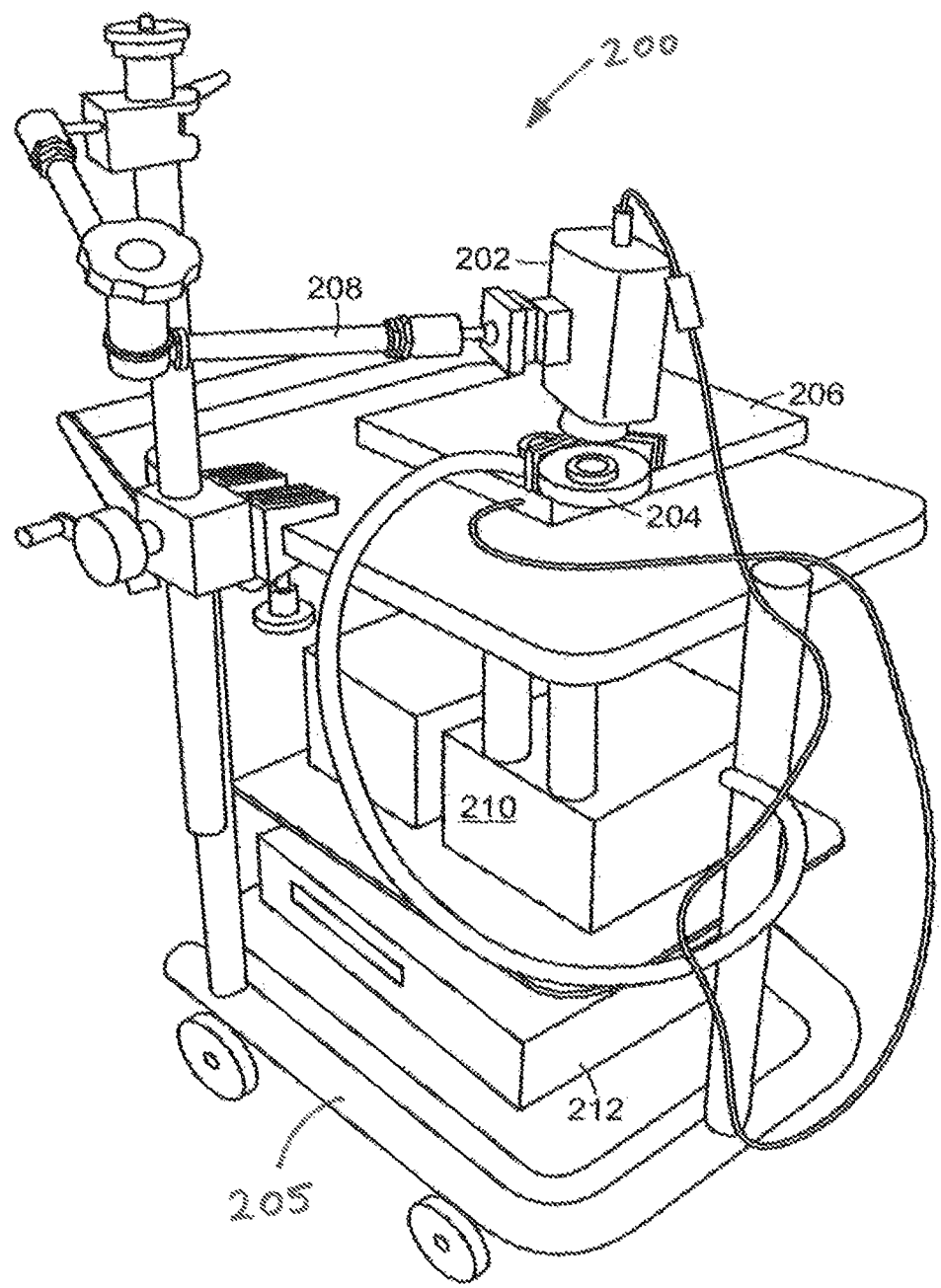
FIG. 2A illustrates a perspective view of a polarization enhanced reflectance imaging instrument in accordance with a preferred embodiment of the subject disclosure.
Figure 2B:
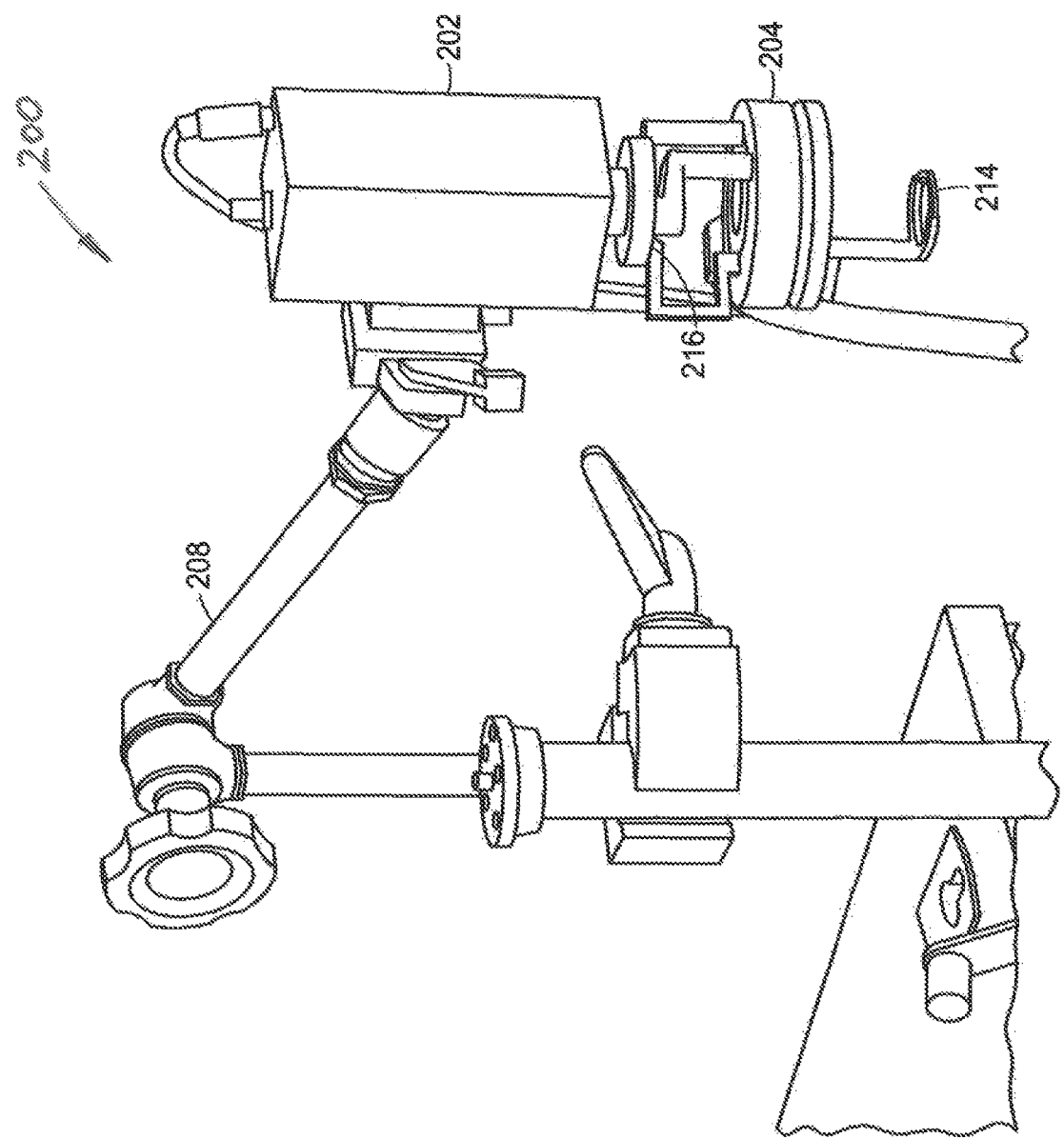
FIG. 2B is a view of the instrument of FIG. 2A including a spacer, an illuminator, an optical lens, a CCD camera, and an articulating arm.

Referring to FIGS. 2A and 2B, perspective schematic views of an instrument 200 in accordance with the subject technology are shown. The instrument 200 includes an imaging instrument comprising a CCD camera 202 and an illuminator 204 mounted on a cart-like structure 205 for easy mobility. The imaging instrument 200 includes processing capability such as an application specific printed circuitry board (ASIC PCB) 206 and/or a computer. The imaging instrument 200 includes an articulating arm 208. The instrument 200 also includes a lamp or illumination source 210 and controller 212 operatively coupled to the ASIC PCB 206.

Referring additionally to FIG. 2B, a close-view of the articulated arm 208 of the instrument 200 is shown. The instrument 200 includes CCD camera 202, illuminator 204, articulating arm 208, spacer 214 and optical lens 216. This instrument 200 allows acquisition of cross-polarized light images at selected wavelengths, including 410 nm, 440 nm, 570 nm, and 650 nm in the visible spectral range. The instrument 200 also provides field of view of up to 50×50 mm and lateral resolution down to the pixel size of the camera 202. In one embodiment, the camera 202 is a high resolution camera with a 0.5× objective lens.

The imager (CCD camera and illuminator) or light delivery and detector elements 10 are installed on the articulated arm 208 to enable flexibility and comfort to the subjects. The spacer 214 has a length approximately equal to the focal length of the objective lens, with a sterile glass plate at the bottom of the spacer 214 to ensure proper focusing distance, flatten the skin surface and to minimize motion artifacts during imaging that can arise from patient movement, such as breathing. A calibrated reflectance reference (not explicitly shown) can attach to the glass plate to enable quantitative assessment of the images. Refractive index matching gel can also be applied to skin surface to reduce refractive index mismatch between skin and glass plate and improve light coupling into the skin and back onto the detector.

The methods, processes, flowcharts and the like described herein illustrate structure and/or logic of the present technology, possibly as embodied in an ASIC PCB coupled to or part of a controller having computer program software for execution on a digital processor, microprocessor and the like. Those skilled in the art will appreciate that the flowcharts illustrate the structures of the computer program code elements, including logic circuits on an integrated circuit, that function according to the present technology. As such, the present technology may be practiced by a machine component that renders the program code elements in a form that instructs a digital processing apparatus and associated components to perform a sequence of function step(s) corresponding to those shown in the flowcharts.

Figure 3:
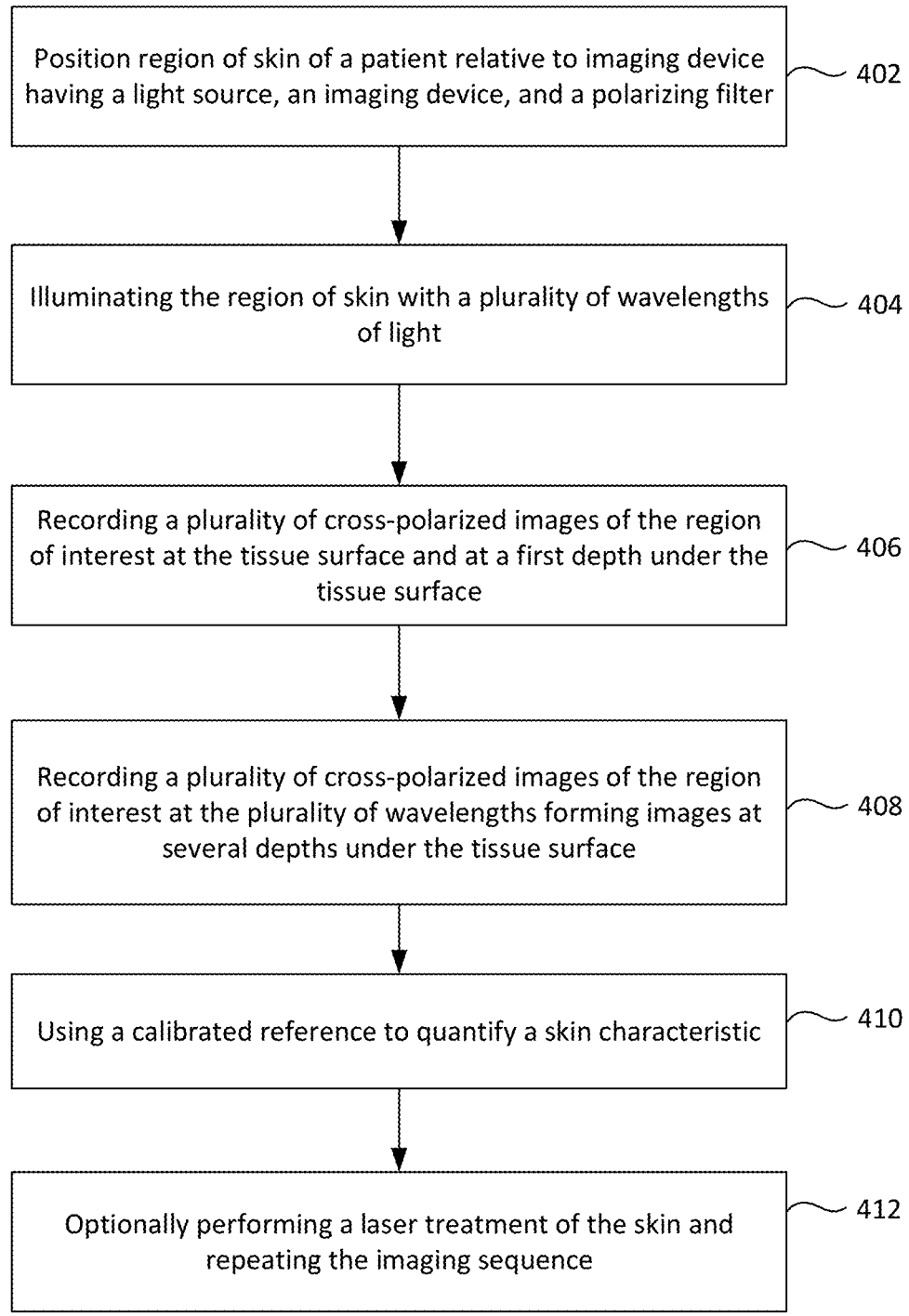
FIG. 3 is a process sequence for performing diagnostic imaging methods in accordance with preferred embodiments of the subject disclosure.

Referring now to FIG. 3, a method 400 for imaging a region of interest on the skin of a patient is shown. At step 402, the user first positions the region of skin relative to the spacer 214, and thereby relative to the light delivery and detector elements 10 to enable the acquisition of polarized images. A holder (not shown) can be used to stabilize the region of skin and the articulating arm 208 can be used to hold the imaging device housing 102.

At step 404, the region of skin is uniformly illuminated to capture an image of the entire field of view in a single shot. At step 406, a plurality of images are recorded at the tissue surface and at a first depth. At step 408, additional images are recorded at a deeper, or second depth by altering the illumination wavelength.

The ASIC PCB 206 and/or the controller 212 process the image data using a calibrated reference and thereby generate quantitative data for a skin characteristic at step 410. Data such as the content and density of collagen, the size of individual collagen bundles and blood vessels is measured. The images can have a field of view that ranges from 3 cm$^2$ to 30 cm$^2$, for example. The instrument 200 can include an adjustable lens assembly to enable changing the area of the field of view. At step 412, the method 400 is used with treatment methods to monitor changes in the skin. One example of a treatment method is laser treatment of the skin.

By being able to monitor and repeat the imaging, variations and changes, both beneficial and not, can be reviewed to enhance treatment protocols.

After acquisition, the images can be filtered using low pass and sharpen filters to reduce the noise and impact of scattering from the lower skin layers (such as lower blood plexus and subcutaneous fat) on the quality of collagen images. Further details regarding instruments and methods of polarized imaging of tissue are described in International Application No. PCT/US2012/025678, filed Feb. 17, 2012, which corresponds to U.S. application Ser. No. 14/000,106 accorded a filing date of Aug. 16, 2013 and published as US 2013/0324846 on Dec. 5, 2013, the entire contents of this application being incorporated herein by reference. Another example of a Polarization-enhanced multi-spectral imaging device is shown in U.S. PGPUB No. 2016/0066833 A1 published on Mar. 10, 2016 to Yaroslavsky et al., which was used to observe and monitor after effects of treatment on skin, the entire contents of this application being incorporated herein by reference.

Figure 4:
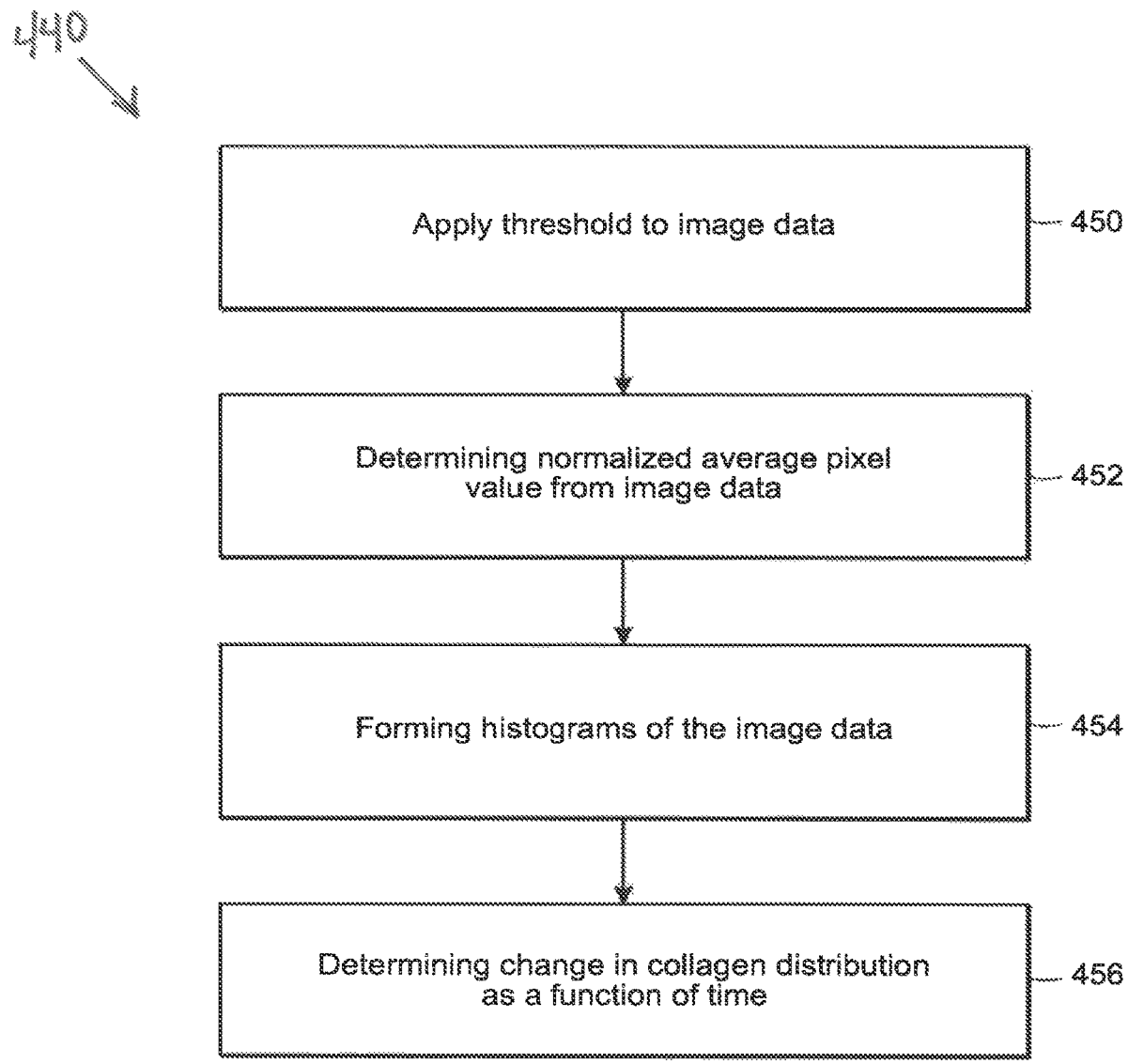
FIG. 4 is a process sequence illustrating an image processing method in accordance with the subject disclosure.

Referring now to FIG. 4, a method 440 for advantageously determining change in collagen distribution over time is shown. The ASIC PCB 206 and/or the controller 212 preferably perform the steps of method 440. In one embodiment, the ASIC PCB 206 and/or the controller 212 are integrated into a single unit. At step 450, a threshold is applied to the image data. The simplest thresholding methods replace each pixel in an image with a black pixel if the image intensity is less than some fixed constant, or a white pixel if the image intensity is greater than that constant. The constant may be determined from reference data related to the patient or a default value set according to a plurality of characteristics such as the patient's age, tumor location, skin tone, health and the like. At step 452, a normalized average pixel value is determined from the image data. At step 454, histograms are formed from the image data. At step 456, changes in the collagen distribution are determined as a function of time such as by variation in the histogram.

Referring to FIG. 5A, a series of images 500a-c represent examples of thresholded region of interest (ROI) images. Image 500a is raw image data of an area of skin. Image 500b is a processed image of image 500a. Image 500b has had a threshold applied to the image 500a so that contrast is increased. Image 500b includes a boxed area 502. Image 500c is a more detailed view of the boxed area 502 with two sets of opposing arrows 504 thereon for illustration in measuring size of collagen bundle. The arrows 504 represent measured collagen at 107 um and 118 um, respectively.

Referring now to FIG. 5B, an intensity histogram 510 of collagen bundles based on a threshold image 512 is shown. From the threshold image 512, collagen bundle size and percentage collagen area are measured. In the example shown, the collagen bundle diameter obtained from the threshold image is approximately 110 µm (see image 500c), which is consistent with sizes reported from historical studies. In some embodiments, the expected collagen bundle diameter for the patient's age is used to determine a proper thresholding level.

In the intensity histogram 510, percentage collagen area, normalized average pixel value of collagen and normalized the full width at half maximum (FWHM) of collagen bundles for subjects in three age groups are summarized in Table 1 below. With regard to Table 1, age group A (28-31 years of age) shows the highest average collagen area, which is 19% higher than age group B (35-40 years of age) and 39% higher than age group C (50-65 years of age). Normalized average pixel value of collagen, which indicates both the density and compactness of the collagen bundles, also shows a maximum value in age group A, and decreased by 5% and 8% in age group B and C respectively. In contrast, the FWHM increases with age as shown in Table 1.

Regarding Table 2 below, data from immunohistochemical measurements comparing the relative quantity of type I and type III collagen from facial skin of subjects ranging from 30 to 80 years old is shown. As can be seen from Table 2, decreasing of the intensity of immune stained collagen with age is consistent with the results obtained from the imaging instruments described herein. In contrast to the immunohistochemical measurements, which used antibodies to investigate the type I and type III collagen, the method of imaging described here enables quantification of the overall collagen density from the image itself.

In contrast to the percentage collagen area, this analysis indicates that normalized FWHM of the intensity histogram of age group A is lower than that of age group B and C by 22% and 25% respectively (Table 1). The increase of FWHM value in skin of the oldest group of patients indicates the decreasing of compactness and reflectivity of the collagen bundles. In younger subjects, the collagen network is more compact, and the space between collagen bundles can hardly be seen in the image. Most collagen bundles have high reflectivity as shown in FIGS. 10A-10F (described below in detail). In younger subjects, histograms of the images are sharp and narrow, which leads to low FWHM. However in elderly subjects, the collagen network starts to become sparse. The space between collagen bundles appears as dark grey in the image. Part of the collagen bundles still preserve high reflectivity while some show low reflectivity. Both the collagen bundles with low reflectivity and degenerated collagen structures appear as dark gray pixels in the image, which results in the broader intensity histogram with long tail and higher FWHM.

Figure 10A:
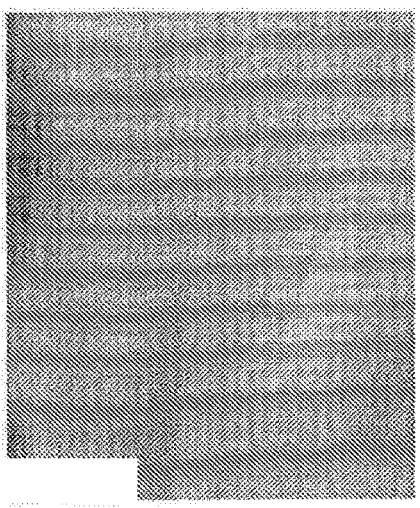
FIGS. 10A-10F show both digital pictures and wide-field ROI images of various subjects.
Figure 10B:
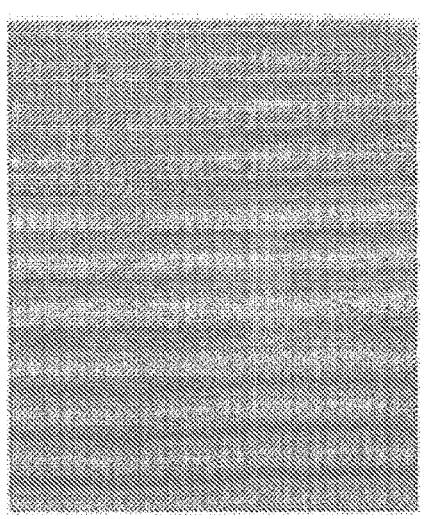
Figure 10C:
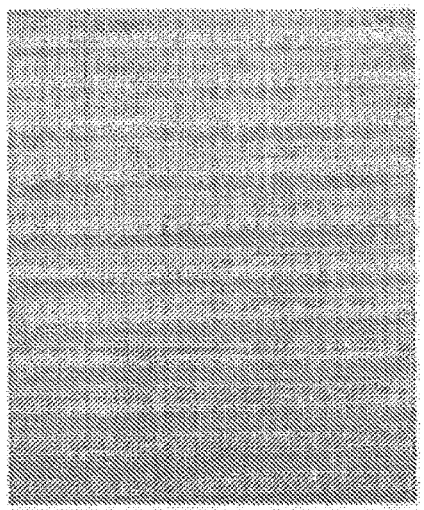
Figure 10D:
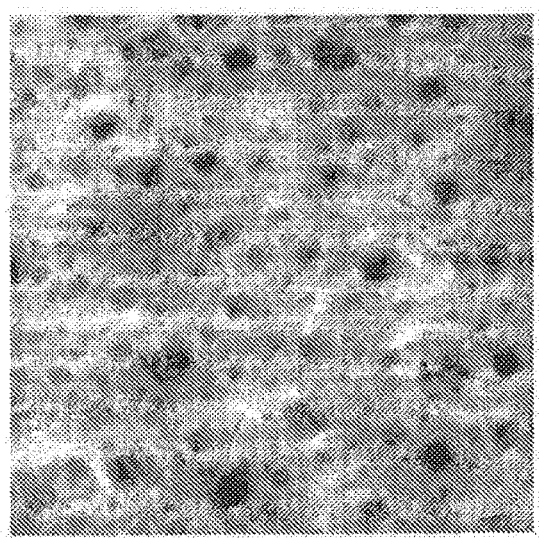
Figure 10E:
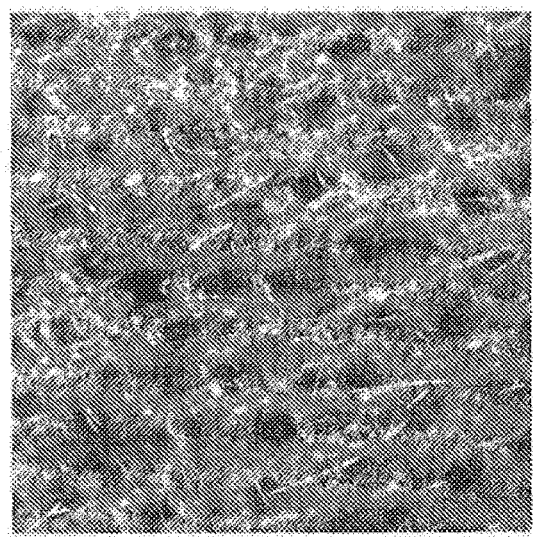

Increased FWHM in senior skin can be measured using second harmonic generation measurements of human facial skin. The various differences in characteristics between young and senior skin can be seen in the images in FIGS. 10A-10F. Note that FIGS. 10A and 10D are images of 25 year old subjects, FIGS. 10B and 10E are images of 35 year old subjects, and FIGS. 10C and 10D are images of 65 year old subjects.

Figure 6:
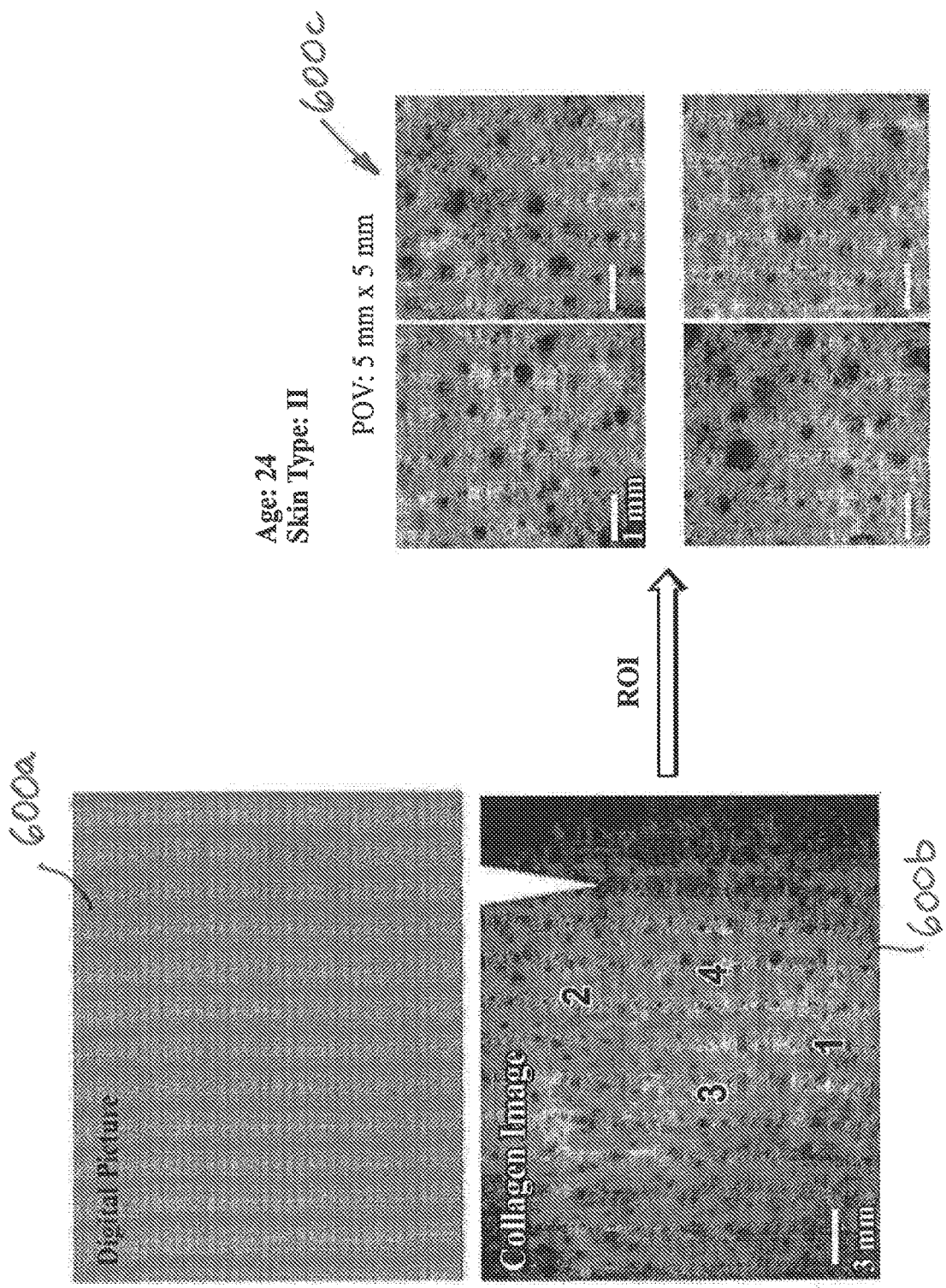
FIG. 6 shows a series of images for a subject including a digital picture of a subject; a 410 nm cross-polarization image; and four indicated regions of interests, respectively.

FIGS. 6 and 7 show example images of 24 and 43 year old subjects, respectively. FIGS. 6 and 7 show a digital picture 600a, 700a of the skin surface, a processed polarization enhanced wide-field reflectance image 600b, 700b, and a composite 600c, 700c of four regions of interest from image 600b, 700b for each subject, respectively. In the 440 nm wide-field reflectance image 600b of the 24 year old subject, the collagen appears bright due to scattering and the spaces in between collagen bundles appear dark, which strengthens the contrast of collagen area. The smaller ROIs with field of view 5 mm×5 mm preserve resolution of 12 µm, which enables quantitative analysis of collagen structure and density. To evaluate dermal structure, the instrument generates data to evaluate the collagen area such as the full width at half maximum (FWHM) of the intensity histogram (see FIG. 5B), as well as normalized average pixel values.

To enable comparison between the subjects, all the images were normalized using calibrated reflectance reference. Histograms of the normalized ROI images were calculated a graphed and their full width at half maximum values (FWHM) were determined using the formula presented below, $$f(x) = \frac{1}{\sigma\sqrt{2\pi}} \exp\left[-\frac{(x-x_o)^2}{2\sigma^2}\right]$$

$$FWHM = 2\sqrt{2 \ln 2}\,\sigma \approx 2.3548200\sigma$$

Normalized ROI images were thresholded to about 35% to 40% brightness. Threshold values were recorded to define percentage collagen area.

Then parameters obtained from different ROIs were averaged over each subject. We summarized the data for each subject and the results demonstrated large variance for subjects of different ages (Shown in FIGS. 6A-C, 7A-C and Table 1). As shown in FIGS. 6 and 7, collagen area, representing collagen density and content, decreases with age, whereas full width at half maximum value, indicating compactness of collagen bundles, increases with age.

TABLE 1

Quantitative Analysis of Collagen. Group A-7 subjects; group B-6 subjects; Group C-3 subjects. Skin types I-III.

| averaged values | group A 28-31 | group B 35-40 | group C 50-65 |
| --- | --- | --- | --- |
| area occupied by collagen, % | 1 | 0.84 | 0.75 |
| normalized APV of collagen | 1 | 0.95 | 0.92 |
| normalized FWHM | 0.75 | 0.97 | 1 |

TABLE 2

Data from immunohistochemical studies comparing the relative quantity of collagen from subjects ranging from 10 to 80 years old, represented by nth decade of age.

| | \multicolumn{5}{c}{Age (decades)} |
| --- | --- | --- | --- | --- | --- |
| | $3^{rd}$ | $4^{th}$ | $5^{th}$ | $6^{th}$ | $7^{th}$ |
| Relative quantity of collagen | 1.0 | 1.1 | 0.78 | 0.81 | 0.63 |

To further characterize the data, a biopsy from the imaged site of one of the subjects provide an excised tissue sample and confocal reflectance images (785 nm) were acquired from the dermal side of the biopsy. The results of comparison of macro-imaging and confocal imaging are presented in FIGS. 8A and 8B, respectively. The results demonstrate similarities in the appearance of collagen network. Confocal mosaic was used as a reference to show the performance of the polarization enhanced wide-field instrument described herein.

Figure 8A:
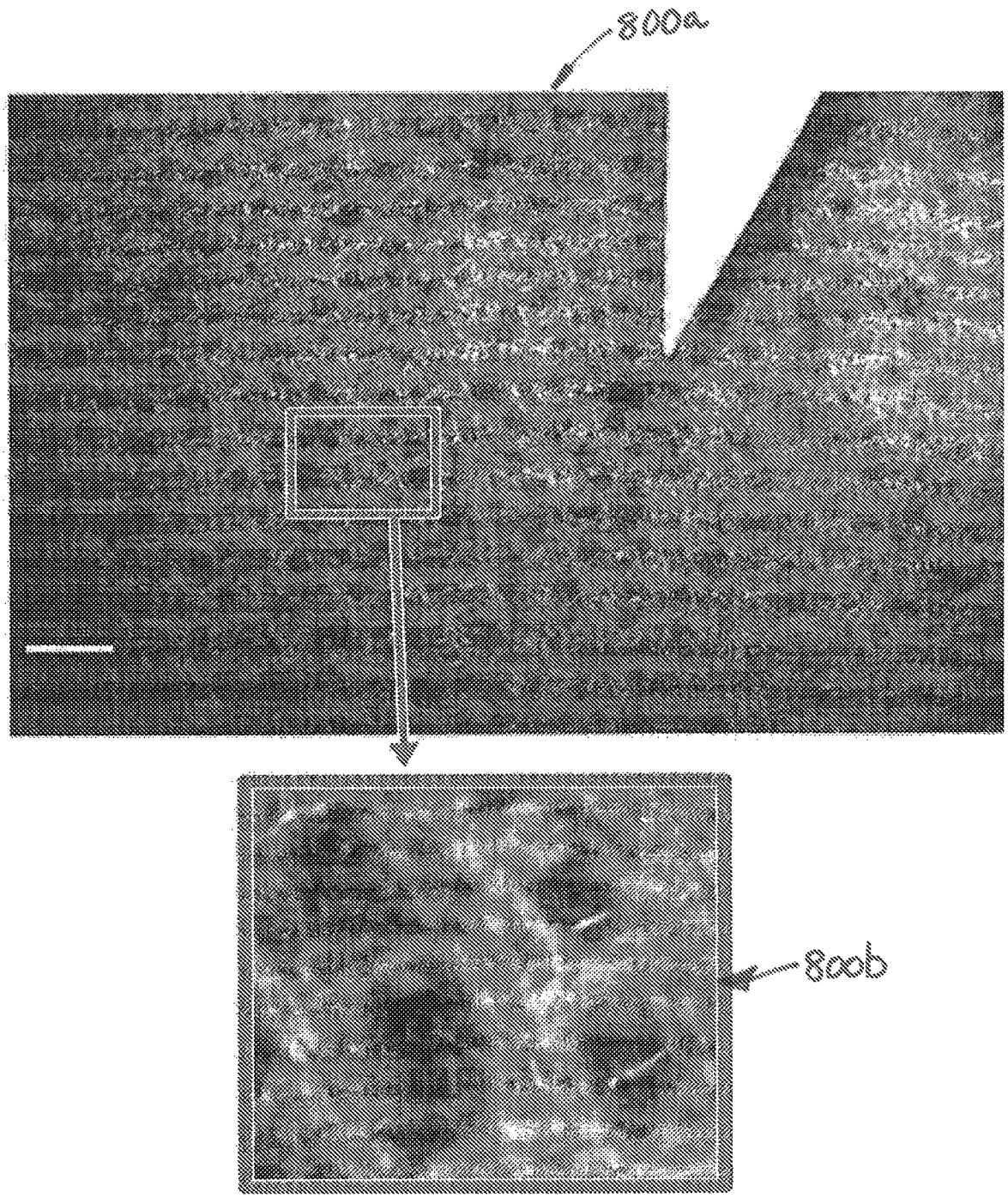
FIGS. 8A and 8B are a comparison of collagen structure revealed by in vivo noninvasive polarization reflectance macro-imaging and ex vivo reflectance confocal imaging.
Figure 8B:
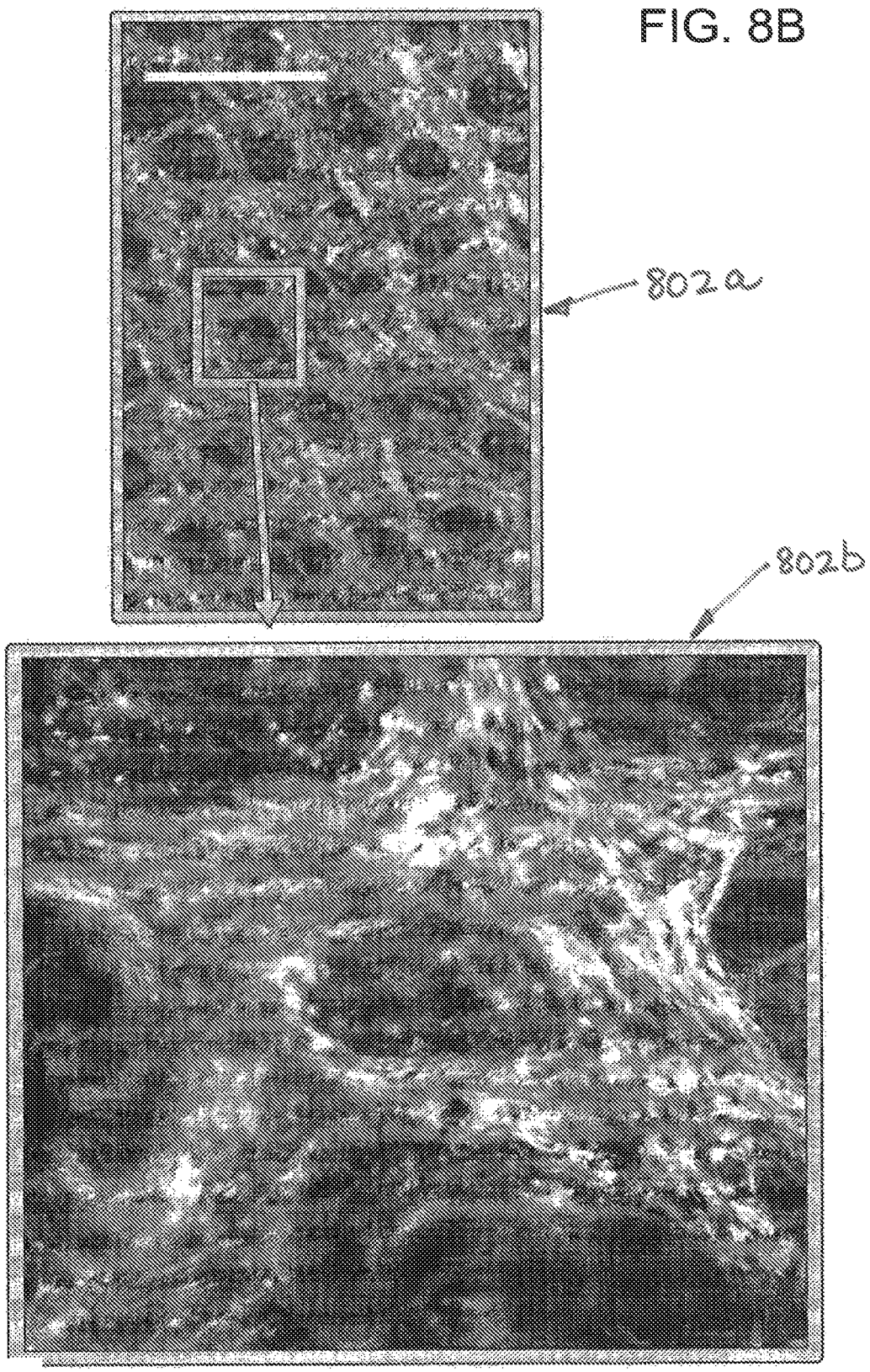
Figure 9A:
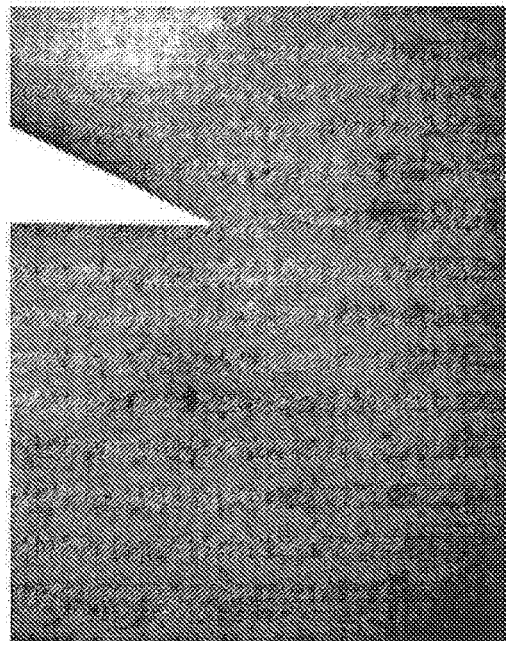
FIGS. 9A-9D show images of a region including a collagen image, an image of blood, a reference image and a photograph of the skin surface, respectively.
Figure 9B:
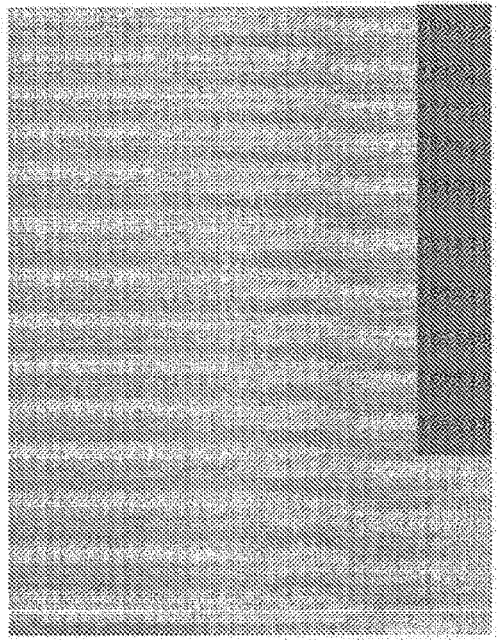
Figure 9C:
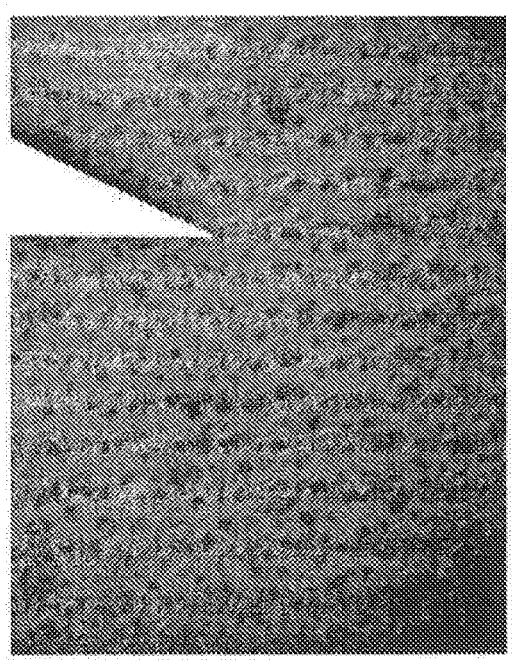
Figure 9D:

FIG. 8A shows in vivo wide-field reflectance images at 440 nm and FIG. 8B shows ex vivo confocal mosaics reflectance images 800a, 800b of collagen. Image 800b is a more detailed view of a portion of image 800a. Similarly, image 802b is a more detailed view of a portion of image 802a. The confocal mosaic was acquired from adjacent single images of the dermal side of the ex vivo skin tissue. The confocal image illustrates the network of collagen fibrils and collagen bundles. Wide-field reflectance images 800a, 800b showed the same pattern of the collagen network as the confocal mosaics 802a, 802b, indicating that the in vivo wide-field image at 440 nm is able to monitor the same level of skin layer as the ex vivo confocal microscopy. With a resolution of 12 µm, the wide-field image delineates the dermal network with the quantified distribution and characteristics of tissue morphology such as collagen bundles and hair follicles.

Detecting cross polarized light remitted from skin allowed for adjusting depth of imaging and rejecting signal from epidermal structures. Depending on the wavelength, as well as type and optical properties of skin, the depth from which images were acquired can vary between about 50 and about 200 microns. The images can emphasize or de-emphasize different skin structures, such as collagen or blood as shown in the photographs in (FIGS. 9A-9D). Fluorescence images can also be obtained to provide additional information regarding distribution of tissue components.

Figure 10F:
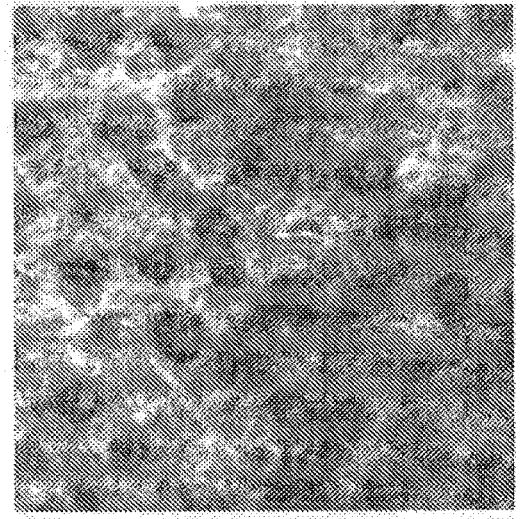
Figure 11A:
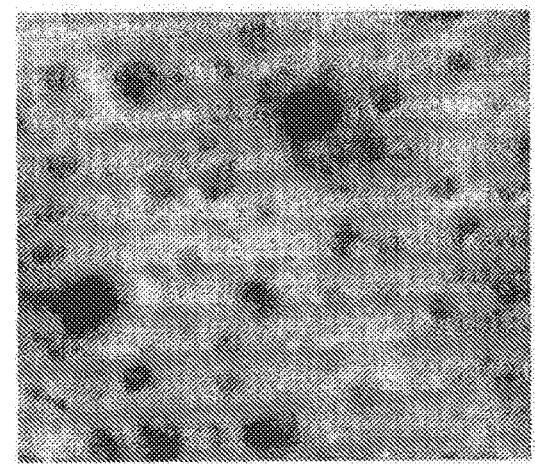
FIGS. 11A-11F show both reflectance and fluorescence images of various subjects.
Figure 11B:
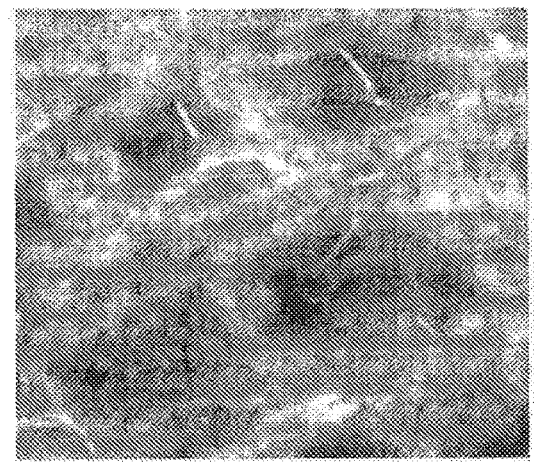
Figure 11C:
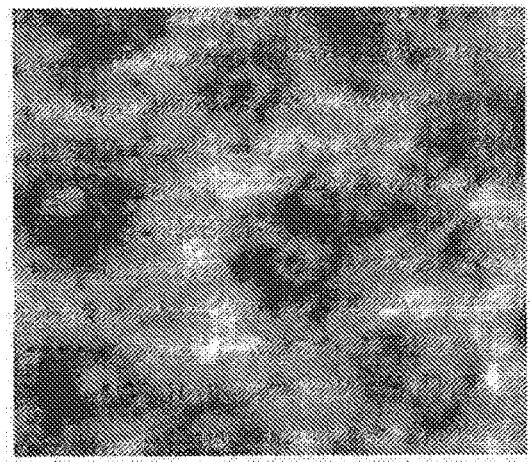
Figure 11D:
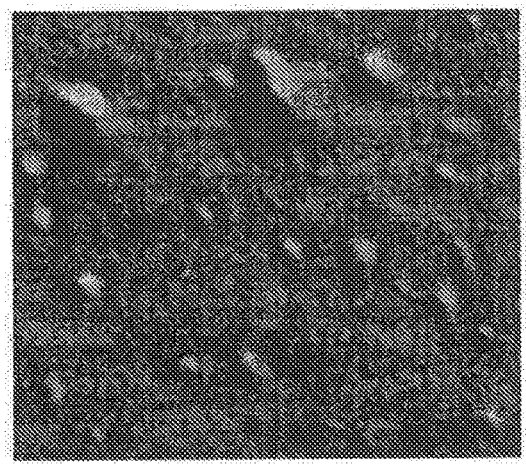
Figure 11E:
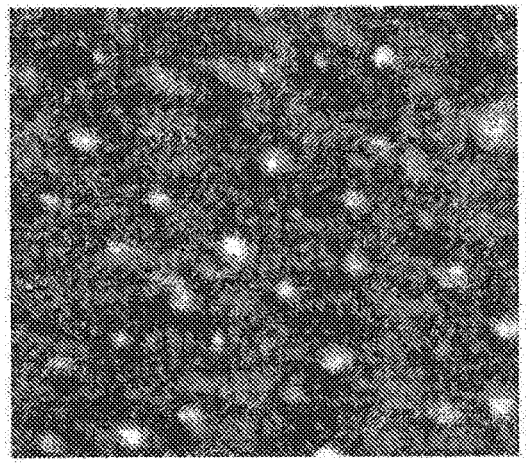
Figure 11F:
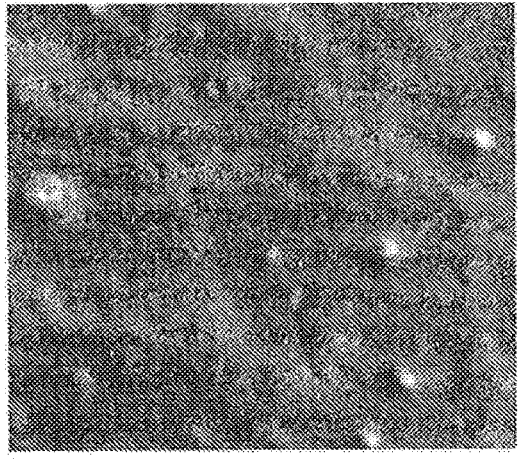

In FIGS. 10A-10F both, digital pictures and wide-field ROI images, of subjects from three age groups with age 25, 35 and 65 years old are shown. FIG. 10A is an image of skin of a 25 year old person. FIG. 10B is an image of skin of a 35 year old person. FIG. 10C is an image of skin of a 65 year old person. FIG. 10D is a wide field image of the collagen structure of a 25 year old subject. FIG. 10E is an image of the collagen structure of a 35 year old subject. FIG. 10F is an image of the collagen structure of a 65 year old subject.

The digital pictures of FIGS. 10A-F provide a macroscopic view of the imaging area, and do not show significant differences between the three subjects, whereas the wide-field ROI image shows distinct variations between subjects with increasing age, indicating a change in density and compactness of the collagen bundles. In the wide-field image of the 25 year old subject (FIG. 10D), the collagen area consists of abundant fine collagen fibers with high reflectivity. The collagen network appears homogeneous and compact over the field of view. The image clearly delineates the margin of collagen bundles and shows high contrast between collagen and non-collagen areas.

In the 35 year old subject (FIG. 10E), the collagen area still preserves a structure, but the overall reflectivity of collagen bundles is reduced in comparison with the younger subject. Interspace between collagen bundles is increased due to the lower collagen density. Some coarse collagen fibers can be seen in the image. The increase of the coarse collagen fibers in senior skin is also present in second harmonic generation measurements. In the image of the 65 years old subject (FIG. 10F), the lower left corner of the image (outlined in black) appears dark grey where the collagen structure is lost. The loss of collagen network appearing in the wide-field image cannot be seen in the macroscopic view (FIG. 10C). Lower contrast between collagen and non-collagen areas and the dark appearance of the collagen area may indicate the degradation of collagen bundles.

FIGS. 11A-11F show both reflectance and fluorescence images of the various subjects in the different age groups.

Figure 12A:
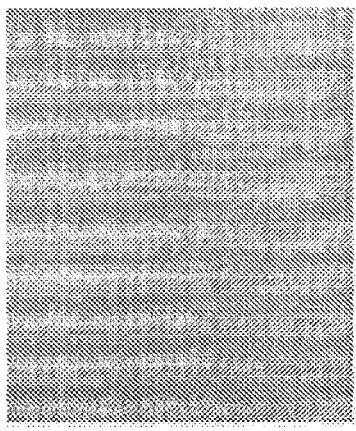
FIGS. 12A-12F show image with the 1 mm bar indicating the size of the area imaged.
Figure 12B:
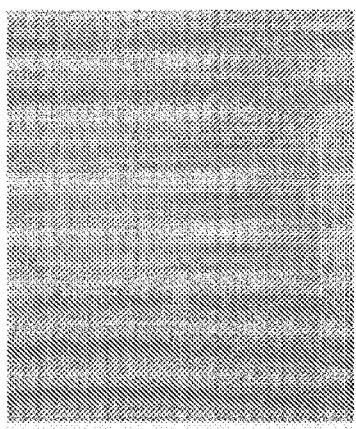
Figure 12C:
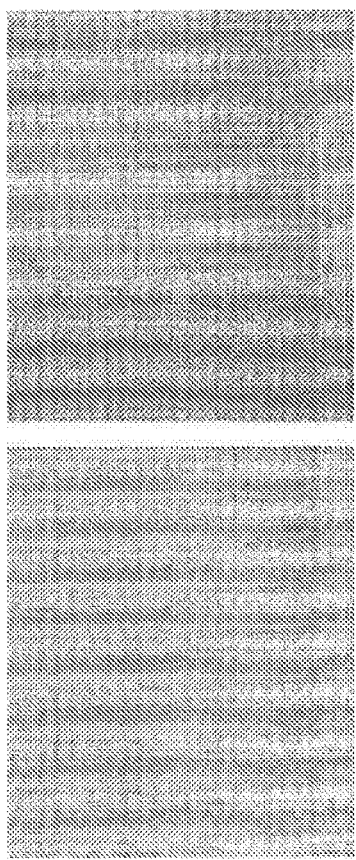
Figure 12D:
Figure 12E:
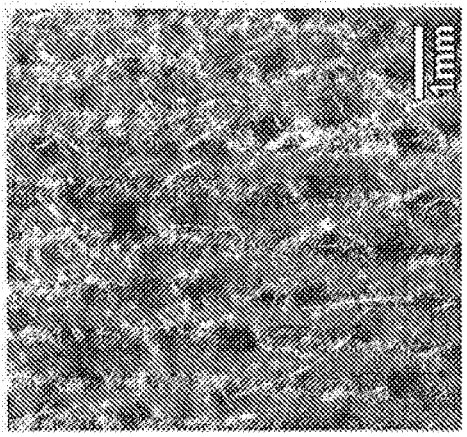
Figure 12F:

FIGS. 12A-12F are images of different aged patients having images that are at least 15 mm$^2$ in area or larger preferably imaging regions having an area of at least 2 cm$^2$ and more preferably at least 4 cm$^2$, thus demonstrating the wide field of view capability of preferred embodiments of the subject disclosure. FIGS. 12A-C are images of the skin of the patients. FIGS. 12D-E are images of the collagen of the patients. As can be seen, the collagen structure changes with age with the effect being a reduction in the brightness of the image.

Figure 13:
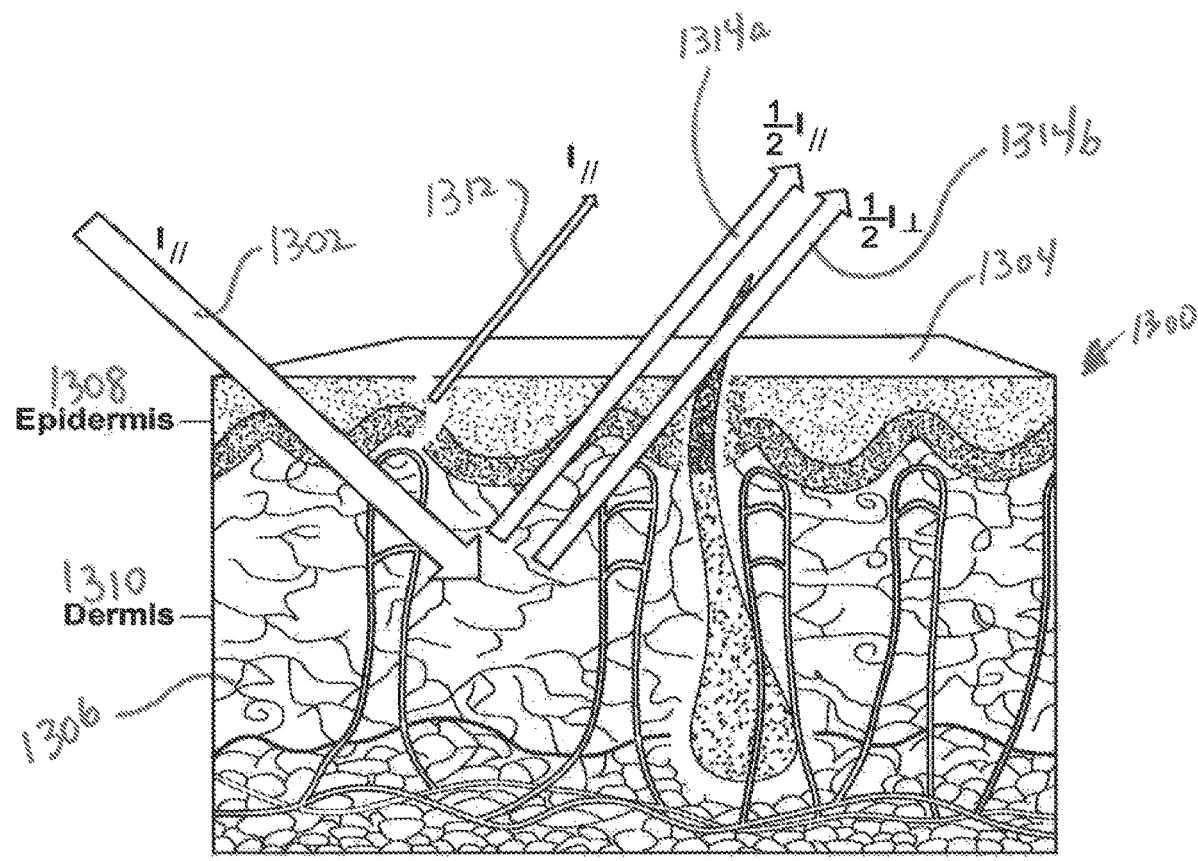
FIG. 13 is a schematic illustrating the effect of polarized light being directed onto a skin surface.

Referring now to FIG. 13, a schematic 1300 illustrating the effect of linear polarized light 1302 being directed onto a surface 1304 of skin 1306 is shown. The linear polarized incident light 1302 is delivered to the epidermis 1308 of the skin 1306. As a result, co-polarized scattered light 1312 is reflected from the epidermis 1308, and random polarized scattered light rays 1314a, 13314b are reflected from the deeper skin layers or dermis 1310.

To obtain the polarized enhanced images of the deeper layers of skin 1306, the light 1312 or signal from the upper skin layers 1308 is eliminated. When applying the linear polarized incident light, back-scattered light from the upper skin layers 1308 keeps the same polarization as the incident light 1302 due to single scattering events. However, as light goes deeper into the tissue, back-scattered light becomes randomly polarized after multiple scattering events. By taking cross-polarized images using the light 1314a, most signals of single scattered light from epidermis and melanin are rejected, increasing the signal to noise level associated with collagen structures.

Light will be attenuated in the tissue depending on the optical properties of the medium, such as absorption and scattering. Between wavelengths of 400 nm and 850 nm, scattering dominates absorption as the main mechanism of attenuation. The imaging depth in tissue is defined as $D=1/\mu_s(1-g)$, where $\mu_s$ is the scattering coefficient and g is the anisotropy factor. In some embodiments, a modified scattering coefficient can be used to approximate the attenuation of both the epidermis layer and the dermis layer. The modified scattering coefficient can be determined by averaging the reduced scattering coefficients of epidermis and dermis.

Figure 14:
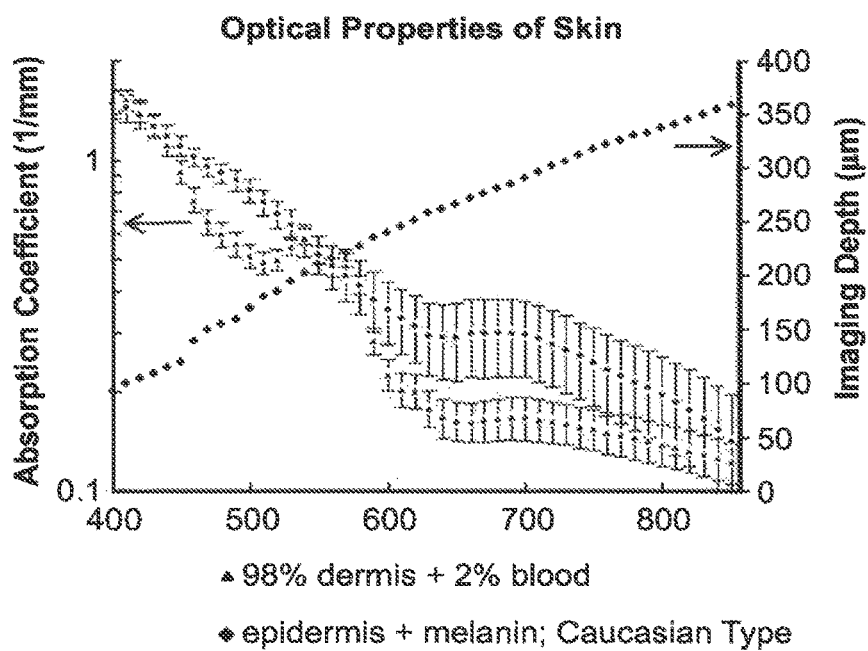
FIG. 14 is a chart illustrating the in vivo absorption of dermis, according to an embodiment.

In FIG. 14, the imaging depths between wavelengths of 400 nm and 850 nm are calculated and graphed. Imaging depths corresponding to the four wavelengths used by the wide-field instrument are shown in Table 3 below.

TABLE 3

| Imaging Depth Calculated for Various Wavelengths | | |
|---|---|---|
| Wavelength | $\mu_s$ (1/mm) | Image below |
| 410 nm | 10.3 | 100 (±10) mm |
| 440 nm | 8.70 | 115 (±11) mm |
| 570 nm | 4.52 | 220 (±25) mm |
| 650 nm | 3.76 | 270 (±31) mm |

At 410 nm, tissue below 100 μm is imaged, at 440 nm tissue below 115 μm is imaged and at 650 nm tissue below 266 μm is imaged. These wavelengths allow for imaging the dermis layer, as the total thickness of stratum corneum and the epidermis layer is approximately 100 μm on average over the human body, even thinner on the facial skin. Absorption in human skin depends on two main chromophores: melanin and hemoglobin. Melanin is produced in epidermis and resides above the basal layers in healthy skin. By taking cross-polarized images, the signal from melanin can be reduced. Hemoglobin from blood mostly resides in the dermis layer. Healthy human dermis layer contains approximately 2% of blood. In vivo absorption spectra of epidermis and dermis between wavelengths of 400 nm and 800 nm are also shown in the graph in FIG. 14. Absorption coefficients at the four wavelengths that can be used by the wide-field instrument are shown in Table 3.

In some embodiments, the following in vivo absorption of dermis can be calculated by adding 2% blood and 98% ex vivo dermis:

$$\mu_{a,di}(\lambda)=2\%\times\mu_{a,b}(\lambda)+98\%\times\mu_{a,de}(\lambda)$$

where $\mu_{a,di}(\lambda)$ is the absorption coefficient for in vivo skin dermis at wavelength $\lambda$, $\mu_{a,b}(\lambda)$ is the absorption coefficient of human blood (hematocrit=44%, 0.3 Osmolality, pH=7.4) at wavelength $\lambda$ and $\mu_{a,de}(\lambda)$ is the absorption coefficient for ex vivo dermis. As shown in FIG. 14, the double-peaked spectra feature around 550 nm corresponds to the blood absorption band. The absorption peak of blood at 570 nm makes it suitable for monitoring vasculature, but not collagen structures.

Figure 15:
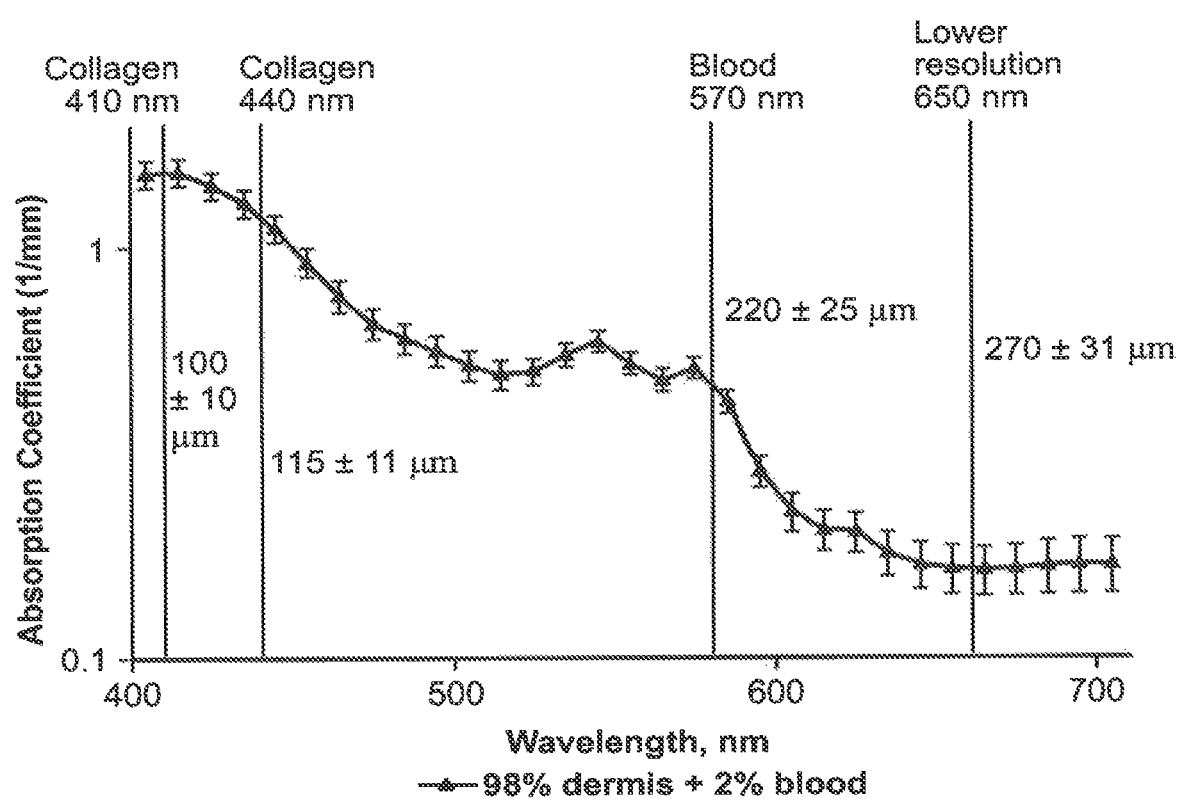
FIG. 15 is a chart illustrating the optical properties of tissue and the dermis absorption coefficient, according to an embodiment.

At a wavelength of 650 nm, image resolution is lower than shorter wavelengths due to the scattering from the bulk tissue. Both images of 410 nm and 440 nm provide proper imaging depth, with lower signal levels from blood and better resolution. However, a wavelength of 410 nm has comparatively higher scattering, which may lead to lower signal to noise ratio than the wavelength of 440 nm. Based on the optical properties of skin between the four wavelengths, cross-polarized reflectance images at 440 nm were used for evaluation of collagen structures. FIG. 15 is a chart illustrating the dermis absorption coefficient for various wavelengths that may be calculated using the formula discussed above.

To enable quantitative assessment of the images and comparison between different subjects, a calibrated reflectance standard (12%-15% for wavelengths in the range of 390 nm-750 nm) was imaged together with the skin area. Images were then calibrated and normalized with the reflectance standard in the field of view. With the reflectivity of the reference and the measured pixel values, absolute reflectance of each single pixel can be calculated and calibrated by the formula $$R_{i,j}^\lambda = \frac{PXL_{i,j}^\lambda}{PXL_{s,ave}^\lambda} \times R_s^\lambda$$

where i, j stand for pixel matrix, $\lambda$ is the wavelength, $R^\lambda_{i,j}$ is the reflectivity of the single pixel (i, j) at wavelength $\lambda$; $PXL^\lambda_{i,j}$ is the pixel value of the single pixel (i, j) at wavelength $\lambda$; $PXL^\lambda_{s,ave}$ is the average pixel value of the reference area; and $R^\lambda_s$ is the reflectivity of the standard reference at wavelength $\lambda$.

Image normalization is the basis for quantitative analysis and enables comparison between different subjects and different images. For each normalized image, low pass and sharpen filters may be carried out with an image processing software to reduce noise and the impact of scattering from the lower skin layers. From each processed image, 4 to 5 regions of interest (ROIs) of 5 mm×5 mm were selected for evaluation.

Figure 16C:
FIGS. 16A-16F show images of the collagen structure taken using various techniques.
Figure 16F:
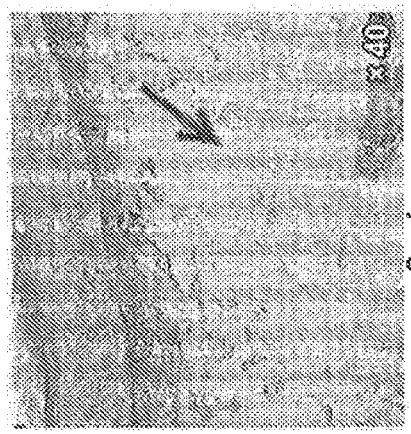
Figure 16B:
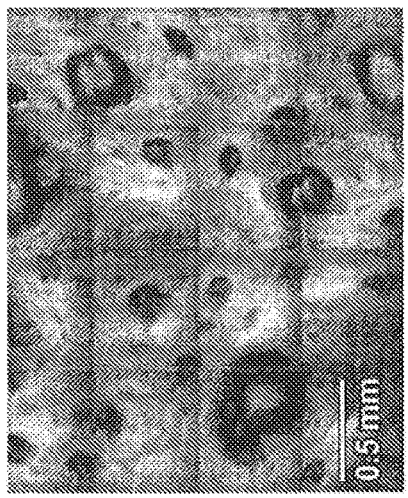
Figure 16E:
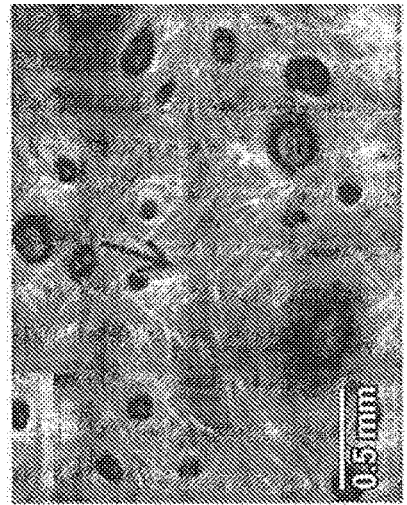
Figure 16A:
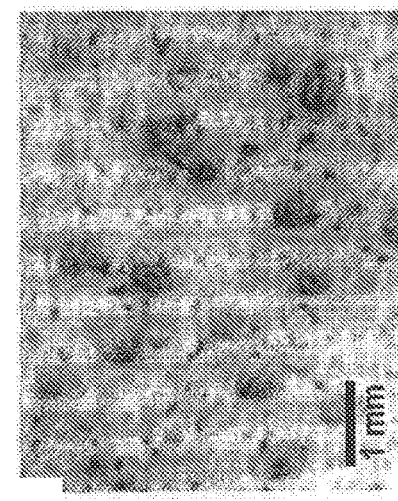
Figure 16D:

FIGS. 16A-16F show images that illustrate the presently disclosed polarized wide-field imaging technique and other techniques that help in evaluating collagen in various subjects. FIGS. 16A and 16D are images of collagen from a young subject and a senior subject, respectively, taken using the polarized wide-field imaging technique described herein. As can be seen, the image of FIG. 16A is relatively brighter than the image of FIG. 16D. FIGS. 16B and 16E are images of collagen from a young subject and a senior subject, respectively, taken using the second harmonic generation technique. FIGS. 16C and 16F are images of collagen from a young subject and a senior subject, respectively, taken using the immunohistochemical technique. FIGS. 16A-16F allows for a comparison between the various techniques, and show the loss of collagen in the senior subject versus the young subject particularly well in this study and the second harmonic generation images.

Figure 17A:
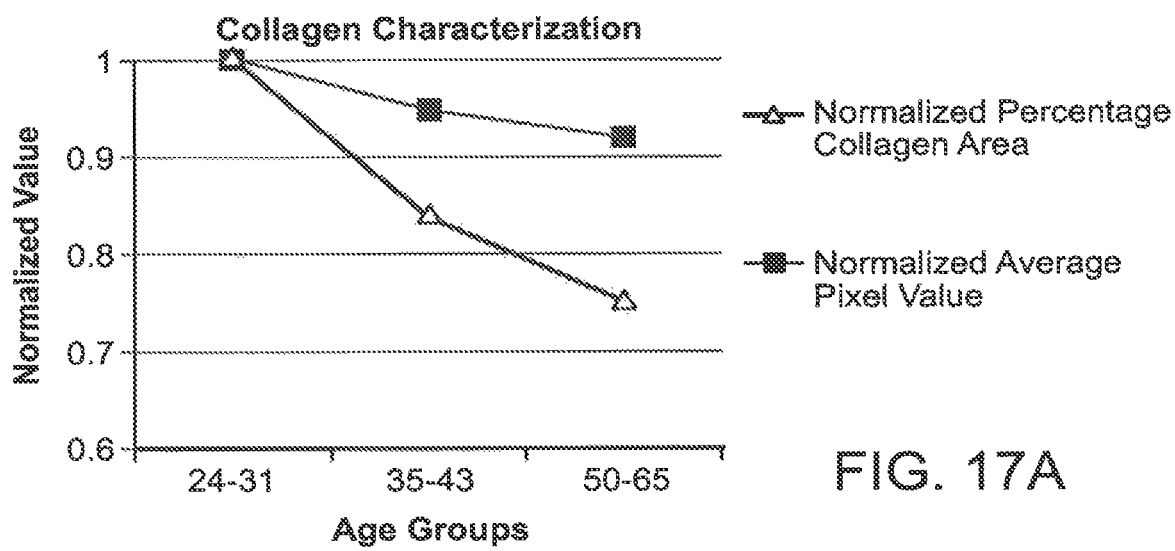
FIGS. 17A-17B are charts illustrating various quantifiable measurements of the collagen structure from different subjects.

FIG. 17A is a chart illustrating collagen structure vs. age determined using the polarized wide-field imaging technique. The values used for this chart are shown in Table 4. As can be seen, the collagen is reduced with aging.

TABLE 4

Percentage of Collagen Area and Normalized Mean or Average Pixel Value (APV) for various age groups.

| | Age Group | | |
|---|---|---|---|
| | A (24-31) | B (35-43) | C (50-65) |
| % Collagen Area | 1 | 0.84 | 0.75 |
| Normalized APV | 1 | 0.95 | 0.92 |

Figure 17B:
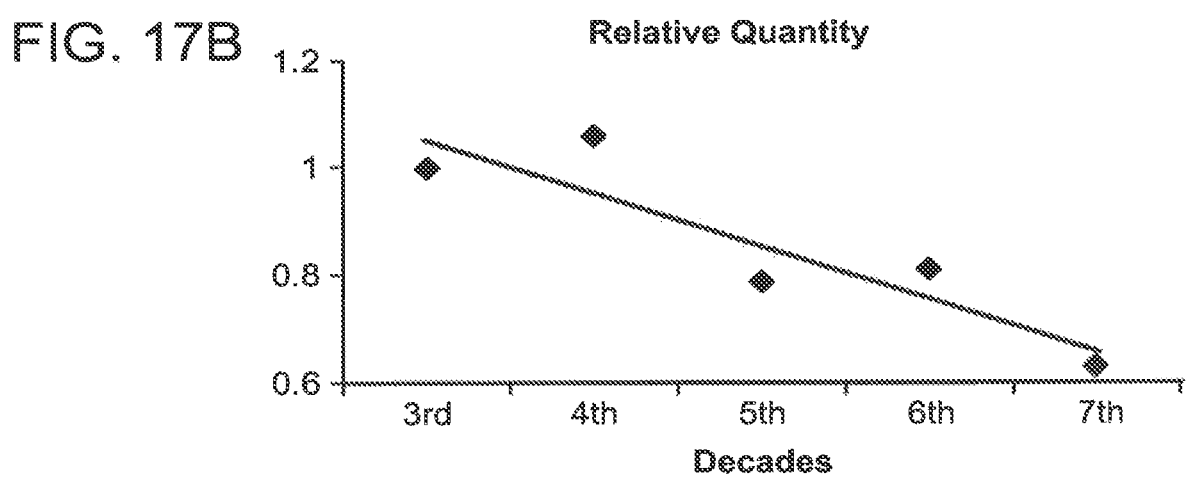

FIG. 17B is a chart illustrating the relative quantity of collagen based on age using an immunohistochemical analysis. The values used for this chart are shown in Table 5.

TABLE 5

Relative quantity of collagen determined from an immunohistochemical study

| | Age (decades) | | | | |
|---|---|---|---|---|---|
| | $3^{rd}$ | $4^{th}$ | $5^{th}$ | $6^{th}$ | $7^{th}$ |
| Relative quantity of collagen | 1.0 | 1.1 | 0.78 | 0.81 | 0.63 |

Both charts in FIGS. 17A and 17B show a decrease in collagen density with an increase in age.

Figure 18:
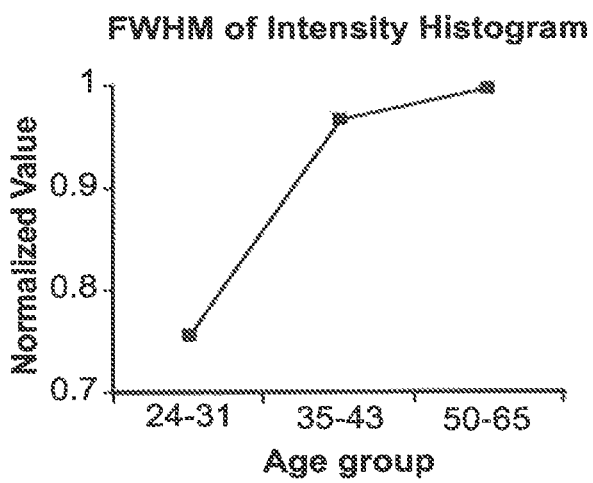
FIG. 18 is a chart illustrating the FWHM vs. age determined according to a preferred embodiment.

FIG. 18 is a chart illustrating normalized FWHM vs. age determined using the polarized wide-field imaging technique. The values used for this chart are shown in Table 6. The chart of FIG. 18 shows an increase in the FWHM with age. This finding is consistent with results from measurements using the second harmonic generation.

TABLE 6

Normalized FWHM for various age groups determined using polarized wide-field imaging

| | Age Group | | |
|---|---|---|---|
| | A (24-31) | B (35-43) | C (50-65) |
| Normalized FWHM | 0.75 | 0.97 | 1 |

The in vivo imaging method provides resolution with a large field of view of at least 1 cm² and preferably at least 8 cm² or more. In a preferred embodiment, a 3 cm×3 cm image is obtained at each depth. The images enable viewing of collagen bundles and detailed dermal structures. Histopathological analysis is the standard for clinical diagnosis, but requires biopsy and can neither be done in vivo nor in real time. The present imaging method provides rapid non-invasive assessment of large skin areas in vivo and is entirely harmless and nonintrusive. Compared to microscopy techniques, such as confocal, two photon and second harmonic, the present imaging method provides orders of magnitude larger field of view combined with a lateral resolution of at least 15 µm and high signal to noise ratio, and does not require expensive components and high power densities of light exposure or laser sources.

Laser non-ablative fractional treatment (NAFT) has become available in a home-use setting due to advent of self-application NAFT devices. In this mode of treatment, in contrast to a typical in-office procedure, fractional coverage is gradually accumulated over a period of time through frequent (e.g., daily) applications. Polarization-enhanced multi-spectral imaging as described herein can be used to observe and monitor effects of the home-administered NAFT on collagen-elastin dermal networks.

Subjects with peri-orbital wrinkles used a commercially available NAFT device (PaloVia® Skin Renewing Laser available from Palomar Medical Technologies Inc., Burlington, Mass.) according to recommended daily treatment regimen. Wide-field reflectance images of both co-polarization and cross-polarization were acquired between 390 and 750 nm. The images were analyzed with a software module in which collagen density, full width at half maximum of image histograms (FWHM IH) and normalized averaged pixel values were calculated to characterize dermal structure.

The images showed detailed dermal structures such as the collagen-elastin network, blood vessel system, and hair follicles. Different collagen network patterns were observed for patients of different age groups. FWHM IH and collagen density data were summarized and used to quantify collagen content. Data analysis at a two-week timepoint after treatment revealed increase in collagen content and ordering of the collagen-elastin network as a result of the treatments. Polarization-enhanced multi-spectral imaging is a useful non-invasive evaluation tool, allowing the monitoring of changes in dermal structure caused by non-ablative fractional treatments.

TABLE 7

| Age Group | Treatment | Collagen Area % | Percentage Improvement % |
|---|---|---|---|
| A (24-25) | pre | 0.91 | 9.89 |
| | post | 1 | |
| B (43) | pre | 0.7 | 24.29 |
| | post | 0.87 | |
| C(50-53) | pre | 0.67 | 7.46 |
| | post | 0.72 | |

Figure 19:
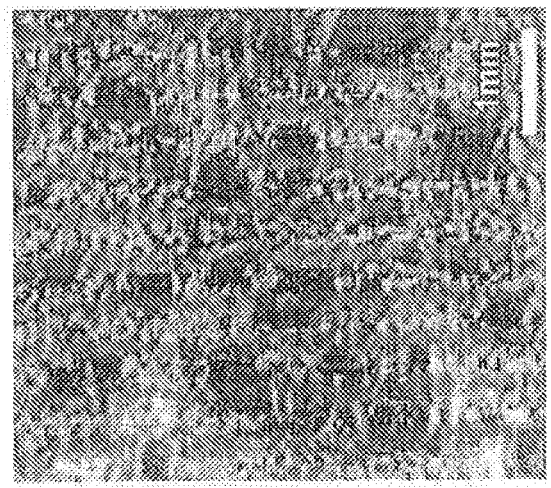
FIG. 19 is an image of the skin prior to treatment.
Figure 20A:
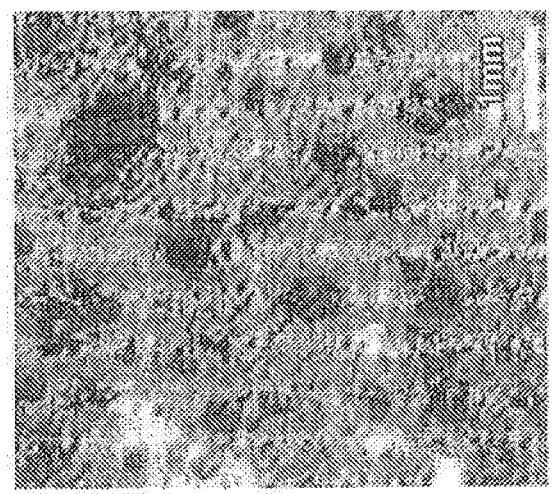
FIGS. 20A and 20B are images of the skin of a patient after treatment.
Figure 20B:
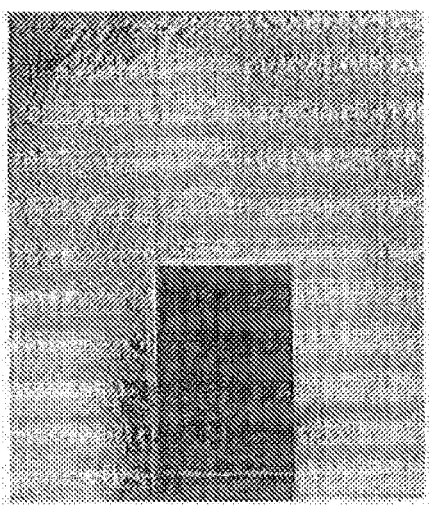

FIG. 19 is an image of collagen of the skin surface prior to treatment. FIG. 20A is an image taken of the same area as shown in FIG. 19 after treatment. The area of treatment is seen in FIG. 20B and demonstrates a substantial increase in the collagen area as a result of the treatment that is seen in Table 7 above.

Age-related changes of facial collagen structure have been measured with different modalities. The immunohistochemical method uses transmission electron microscopy to investigate the skin collagen, which shows the fragmentation of fibers and decreased collagen density by the 6th and 7th decade of life. Confocal laser scanning microscopy and optical coherence tomography can be used to investigate the age-related dermal changes in location and structure of collagen fibers in vivo. These techniques indicate that younger skin consists of relatively thicker collagen bundles than the senior skin. Second harmonic generation microscope images show that thin collagen fibers greatly reduced in elderly subjects, and coarse collagen fiber appears in senior skin. These collagen structural changes can also be seen from the wide-field images described herein. A polarization-sensitive OCT methodology for imaging collagen shows age-dependent decrease in the birefringence of the cheek collagen. These changes in structure, abundance and birefringence of collagen indicate the degeneration and disorganization of collagen fiber in senior skin, which are also indicated by the wide-field images described herein.

The polarization enhanced multispectral wide-field imaging of the present disclosure enables in vivo noninvasive visualization of human dermal structure. Image analyses of collagen density, normalized average pixel value and FWHM show important physiological parameters that reveal the differences in skin with increasing age.

Preferred embodiments provide a polarization enhanced multispectral wide-field reflectance imaging method that is suitable for noninvasive in vivo assessment of dermal structure. Reflectance skin images of subjects between 24 and 65 years old were acquired and analyzed. In comparison with clinical studies that often take several months to complete, the imaging technique described here enables real-time image acquisition and analysis. It enables the rapid overview of a large skin area up to 5×5 cm$^2$ without biopsy or laser exposure. The present disclosed instrument is sensitive to dermal structural differences and provides accurate diagnostic information for subjects with skin type I to III.

Collagen is the major protein in human dermis and contributes heavily to the functional strength of skin as noted herein. Type I collagen forms a regular, three-dimensional, lattice-like structure in the dermis. The collagen lattice structure is commonly effaced by normal aging, photodamage, traumatic injury, and, occasionally, skin cancer and other factors. Tumors perturb the collagen network by both physically displacing collagen fibers and by secreting matrix metalloproteases that degrade the quaternary protein superstructure. Simply put, as tumors grow, the tumors physically damage and displace collagen to deform the stereotypical lattice-like structure.

It has been determined that in the presence of basal cell carcinoma, the disruption of the collagen network produces a localized darkening in the in vivo reflectance image. Darkening in the image co-localized with the tumor at the surgical margin occurs. Providing detailed images illustrating this phenomena to a Mohs surgeon helps identification of a proper surgical margin to encompass the area with disrupted collagen and a positive histologic margin may be avoided resulting in fewer surgical stages needing to be harvested.

One embodiment of the subject disclosure uses a polarization-enhanced wide-field reflectance imaging instrument and methods to image the collagen structure and dermal changes as described previously herein and employing the following methodology. The approach is suitable in vivo to allow rapid assessment of large skin areas with optical sectioning capability of invasive neoplasms such as basal cell carcinoma and squamous cell carcinoma.

Figure 21A:
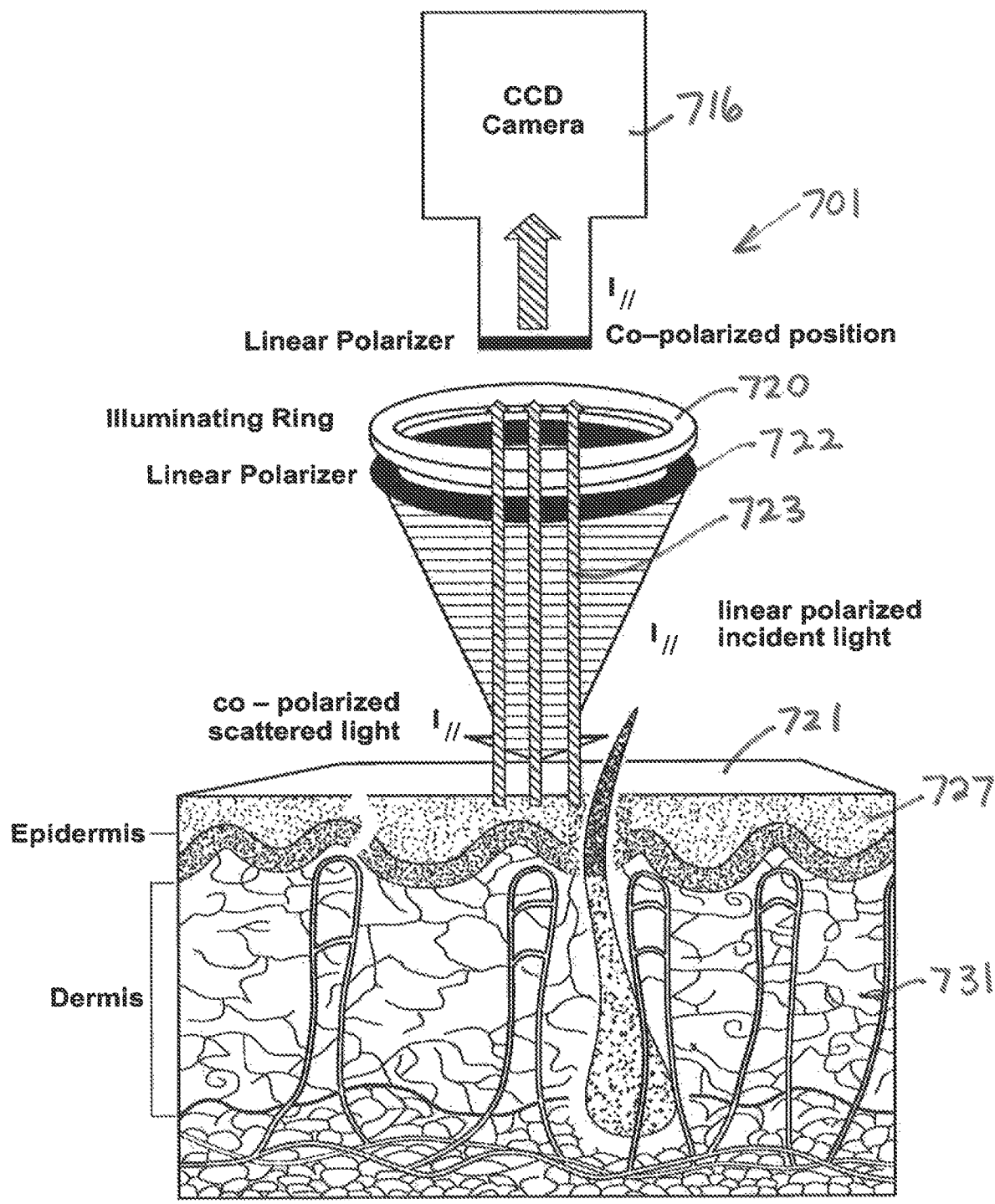
FIGS. 21A and 21B schematically show an instrument obtaining polarized images of tissue.
Figure 21B:
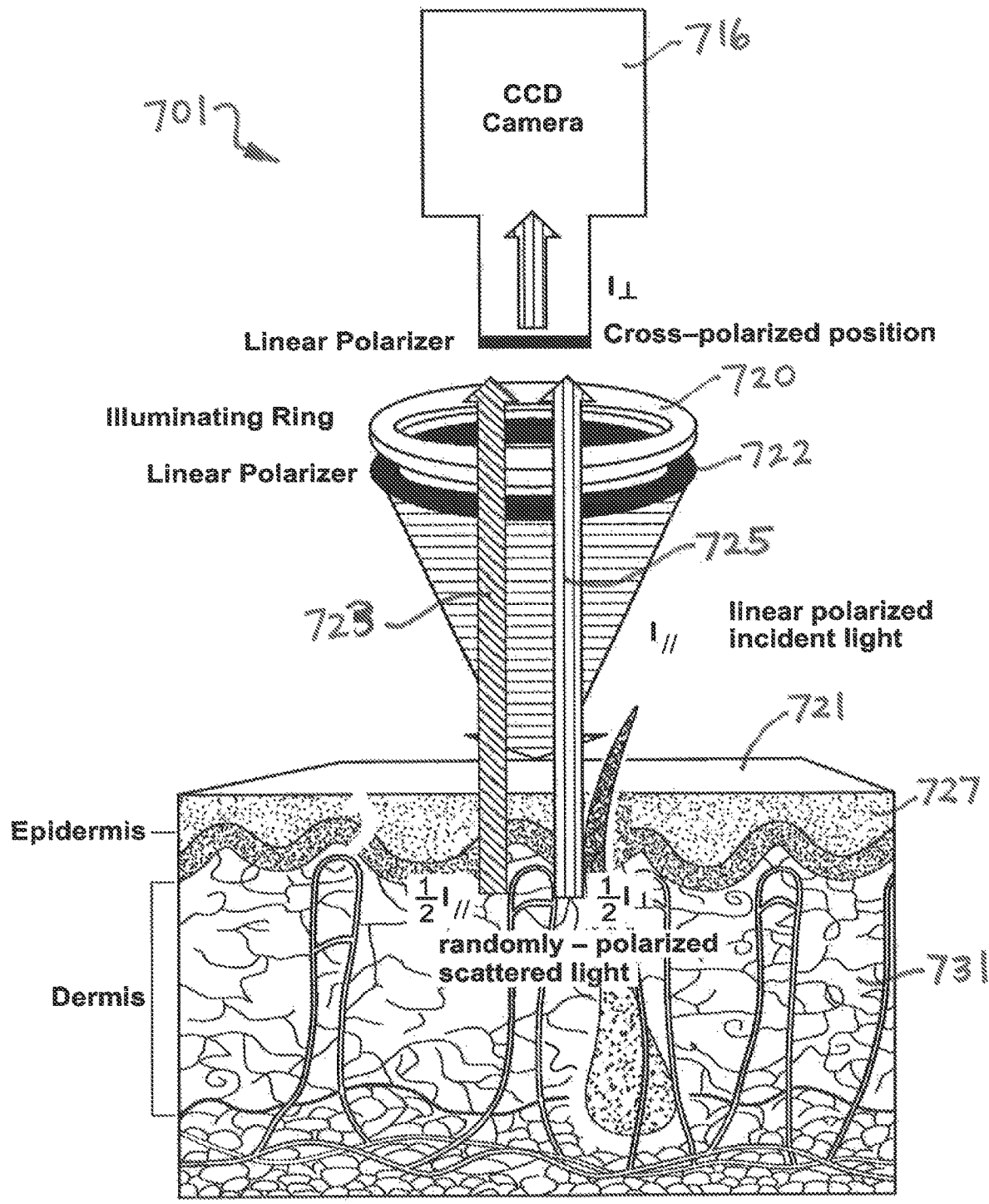
Figure 22A:
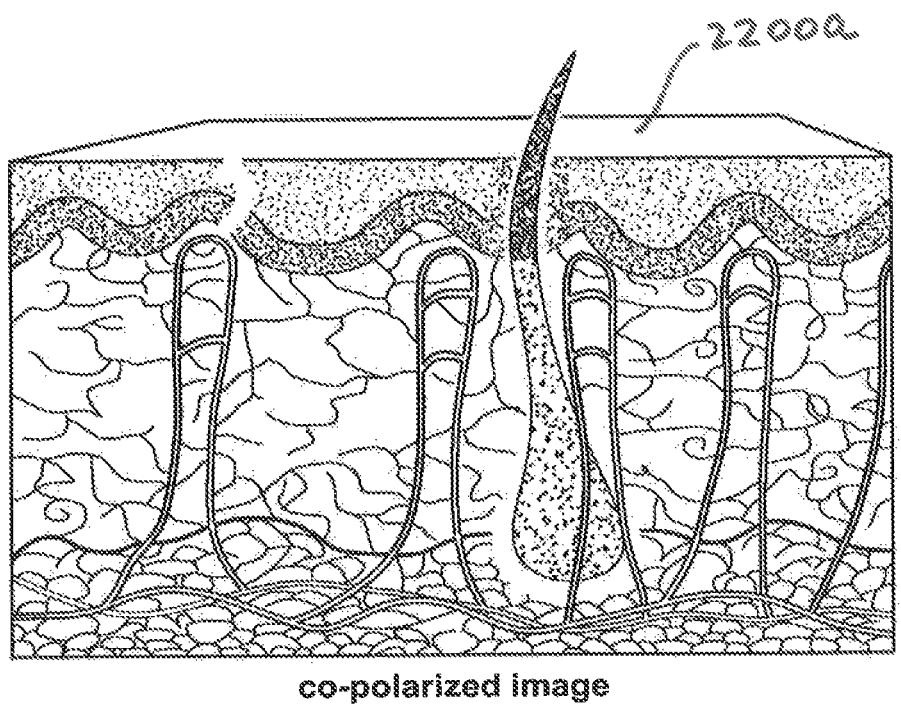
FIGS. 22A-22C show various images of skin tissue using the instrument of FIGS. 21A and 21B.
Figure 22B:
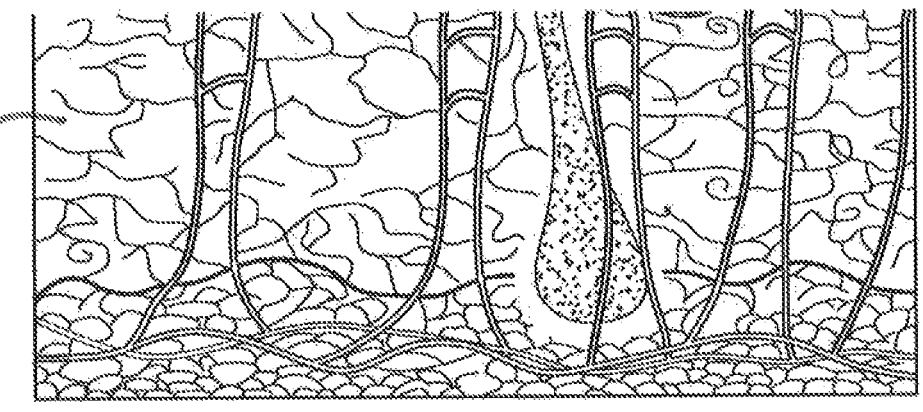

As described above, an imaging instrument 701 records polarized images of tissue in response to illumination from a light source or illumination ring 720 as shown somewhat schematically in FIGS. 21A and 21B. The illumination ring 702 preferably illuminates a section 721 of skin in vivo. A linear polarizer 722 couples to the illumination ring 702 so that linearly polarized light is delivered to the skin section 721. FIG. 21A illustrates, in further detail, a first polarization component of co-polarized light 723 is detected by the CCD camera 716. The components are selected and arranged so that co-polarized scattered light 723 forms the recorded image 2200a such as shown in FIG. 22A. FIG. 21B somewhat schematically illustrates, in further detail, a second polarization component of cross-polarized light 725 being detected by a CCD camera 716. The components are selected and arranged so that cross-polarized scattered light 725 forms another recorded image 2200b such as shown in FIG. 22B. As can be seen in comparing FIGS. 21A and 21B, the cross-polarized light 725 is reflected from the dermis 731 rather than the epidermis 727 of the skin section 721.

Preferably, the instrument 701 is a wide-field, non-invasive imaging device wherein the illumination ring 720 emits narrow band linearly polarized light with full-width at half-maximum of 10 nm in the wavelength range between 390 nm to 730 nm and captures co- and cross-polarized reflectance images. More particularly, the instrument 701 delivers light centered at 440 nm and 640 mm via linearly polarizing fiber optic ring-light illuminator available from Edmunds Optics in Barrington, N.J. 440 nm light is particularly useful to provide adequate depth and resolution for imaging dermal collagen and 640 nm wavelength light allows for the visualization of the blue or purple marker used by the surgeon to outline the lesion boundaries. The camera 716 is available from a Cool SNAP Monochrome Photometrics from Roper Scientific of Tucson, Ariz.

As shown for example in FIG. 2B, the ring illuminator 720 is mounted on an articulating arm with a spacer in place to ensure appropriate focus and to allow flexibility in imaging various anatomic locations. In one embodiment, OPI provided a 4 cm$^2$ field of view, an approximate imaging depth of 100-400 μm, and incident power density below 0.38 mW/cm$^2$. This power density is harmless to the human skin and eyes and is well below the maximum permissible exposure determined by the American National Standards Institute (ANSI). In one embodiment, monochromatic blue light can be used to illuminate the tissue.

Figure 22C:
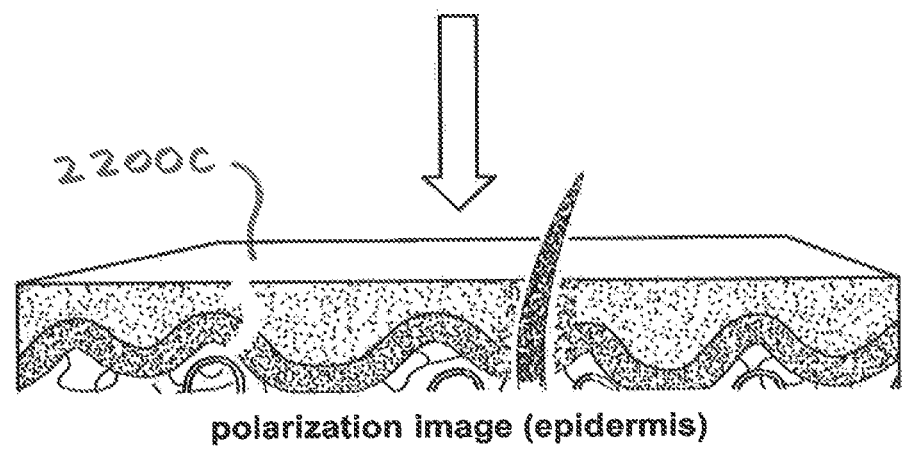

Referring to FIG. 22C, another image 2200c of the tissue is generated for display to the surgeon which can indicate the variation in collagen structures within the selected field of view. The image 2200c is a composite image formed by subtracting the cross-polarization image 2200b from the co-polarization image 2200a.

Figure 23:
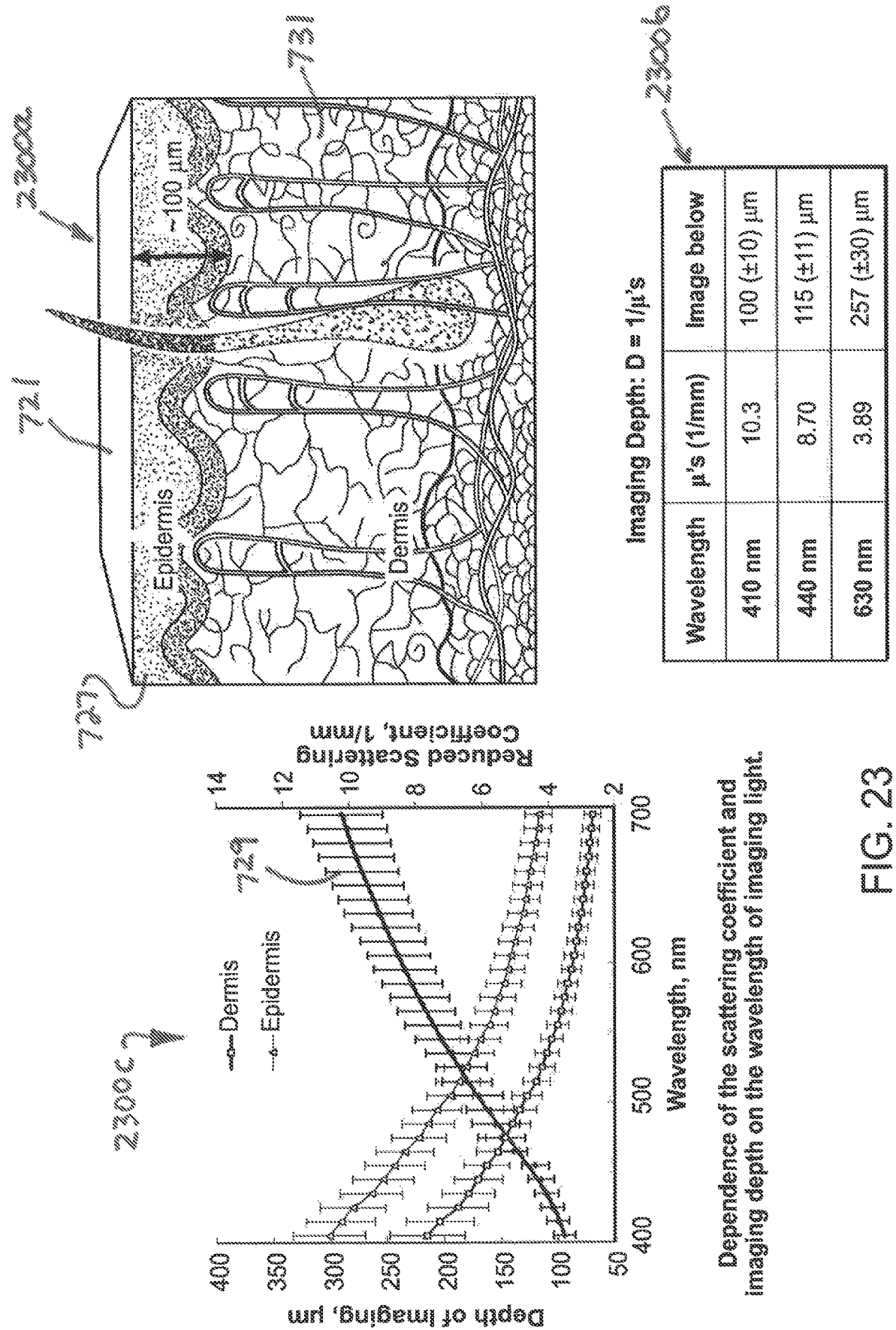
FIG. 23 shows a section of skin in schematic cross-section, a table of illumination wavelengths and the associated imaging depths, and a graph of the wavelengths versus depth of imaging in accordance with the subject technology.

Referring now to FIG. 23, three related depictions 2300a-c are shown to illustrate how selection of illumination wavelengths can determine characteristics of the tissue 721 at different depths. In the tissue 721 of depiction 2300a, the epidermis 727 is about 100 microns thick. Table 2300b illustrates how various illumination wavelengths (e.g., 410 nm, 440 nm, 630 nm) can be selected to optically section the tissue within the epidural layer and underneath the epidural layer (e.g., the dermis) at a plurality of depths. The variation of scattering coefficient (e.g., 10.3, 8.70, 3.89) and imaging depth (e.g., 100 um, 115 um, 257 um, respectively) is a function of the illuminating wavelength.

Graph 2300c is a graph of depth of imaging and reduced scattering coefficient against the illumination wavelength. As can be seen for the dermis and epidermis, the reduced scattering coefficient decreases as the illumination wavelength increases. Also, the depth of imaging 729 increases as the illumination wavelength increases. It is noteworthy that the 100 um depth would depict the epidermis and the dermis. The 257 um depth may be too deep so that the typical tumor is not shown. However, the 115 um depth would typically image the collagen structure very effectively so the surgeon could have an improved idea of the size and shape of the tumor due to the disruption (i.e., darkening) of the associated image.

Figure 24E:
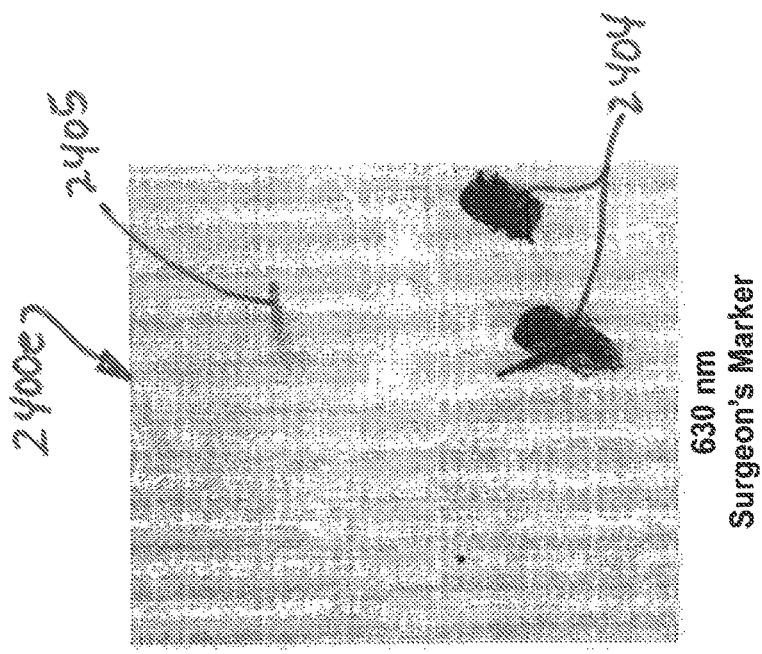

Referring now to FIGS. 24A-E, a graph and several images are shown to illustrate how a surgeon would utilize a marker to define the margin for removal of a tumor. FIG. 24A is a graph 2400a of absorption coefficient against wavelength. Again, the absorption coefficient decreases as wavelength increases. It is noteworthy that blood, which would have peaks between 500 and 600 nm, is not going to be prevalent in the images. As a result, the features of interest are very readily seen in the selected wavelengths.

FIG. 24B is a raw image 2400b acquired of the surface of tissue in vivo. The image 2400b includes two dashes 2404, which are part of a dashed line drawn by the surgeon around a melanoma based on visual inspection. The surgeon marker 2404 is used to define the margin for the removal of tissue including the tumor. The surgeon marker 2404 denotes an area for incision below the dashed line in image 2400b.

Figure 24D:
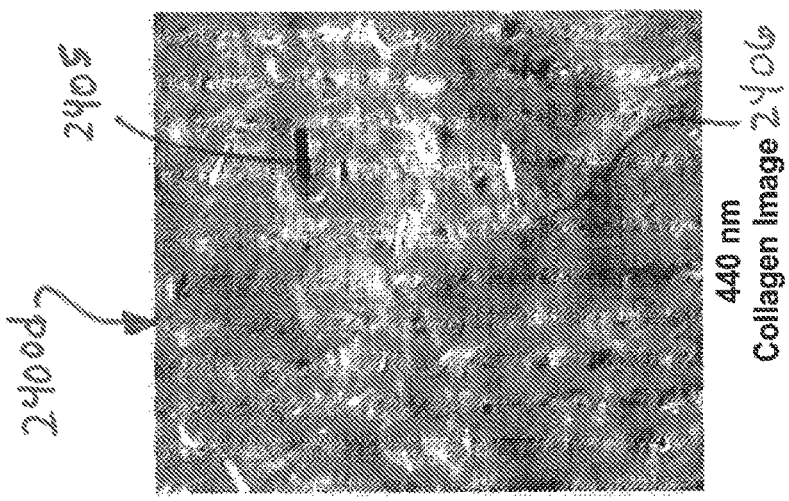
Figure 24C:
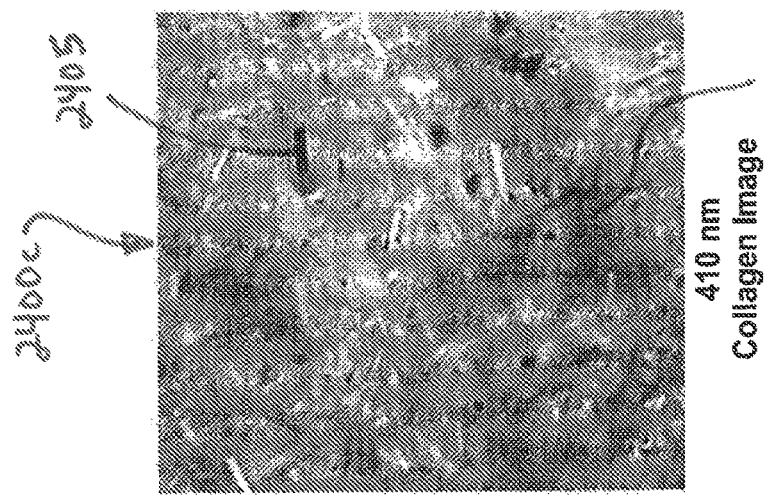

In contrast, FIGS. 24C-E are in vivo processed images 2400c, 2400d, 2400e of the same area at wavelengths of 410 nm, 440 nm and 630 nm, respectively. Images 2400c, 2400d show a darker area 2406 that indicates a disruption in the collagen structure/presence of melanoma. As can be seen, the dark area 2406 extends above the surgeon's marks 2404. The images 2400c-e also includes an improved dash 2405 more accurately indicating a proper excision area with the hope of resulting in a negative margin. It is noted that although image 2400e does not show the disruption caused by the tumor because of the depth of the image being below the tumor, this in itself is useful information. Additionally, the location of the surgeon marker 2404 done by visual inspection can be seen so that comparison with the other images 2400c, 2400d is helpful for making sure that the improved dash 2405 is in a proper location. Thus, based upon the varying depth of the images 2400c-e, the surgeon can more accurately visualize and determine a shape of the tumor by the changes in the collagen structure in vivo. As a result, the procedure will be more effective and efficient.

Figure 25:
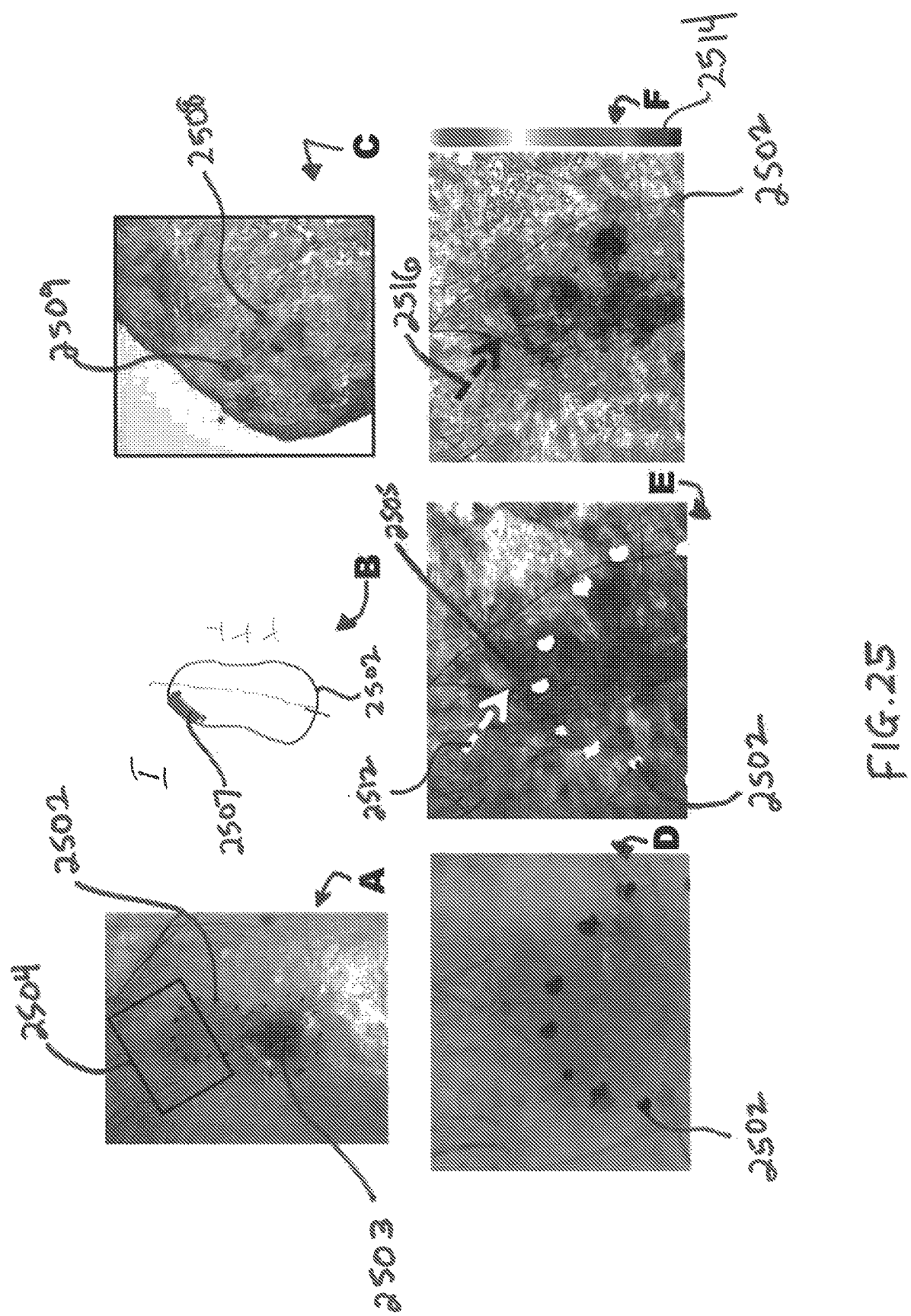
FIG. 25 is a series of images illustrating a process for improving the surgeon marker of a tumor in accordance with the subject technology.

Referring now to FIG. 25, a series of images A-F that illustrate a margin selected by the surgeon with the surgeon marker. The images A-F demonstrate how the subject technology improves upon the prior art visual methods.

Image A of FIG. 25 is a preoperative photograph with a dotted margin line/surgeon marker 2502 drawn in by the surgeon around a tumor 2503. Area 2504 of the preoperative photograph is zoomed in on and shown in more detail in image D. Even with zooming in image D, it is difficult to determine an optimum margin line visually. Thus, when relying upon the visual surgeon marker 2502, the surgeon has a poor guide during the procedure. In fact, surgery was performed using the surgeon marker 2502 so that image B is an intraoperative Mohs map, wherein the solid area 2507 was determined to be a positive margin upon analysis of the excised tissue.

Referring now to image C of FIG. 25, intraoperative histopathological findings (high-power), centered and rotated to overlap the Mohs map in image B is shown. An arrow 2508 points to an island 2509 of basal cell carcinoma in the dermis.

Referring now to image E of FIG. 25, a cross-polarized image taken with illumination at 440 nm is shown. The field of view is 2 cm×1.5 cm. The original margin line 2502 is shown in white cutting through the tumor, which shows as a darker area 2505 pointed out by arrow 2512. The original margin line 2502 was acquired at 640 nm and superimposed on image E. As can be seen, an improved margin line could have been drawn around the tumor as a guide if the image E had been utilized in vivo before excision.

Referring now to image F of FIG. 25, a preoperative 440 nm cross-polarized image with a field of view is 1.5 cm×1 cm is shown. A plurality of dots identify the surgeon marker 2502. A contrast bar 2514 is shown at the right side of image F with light contrast regions corresponding to normal tissue. Dark contrast regions correspond to areas of maximal breakdown of the collagen, and hence the presumptive area of tumor involvement. The black arrow 2516 points to the tumor-involved area extending beyond the excision site and original surgeon marker as was actually confirmed by Mohs surgery histopathology in this case. Thus, the subject technology provides the surgeon with guidance as to how to draw an effective surgeon marker.

Figure 26:
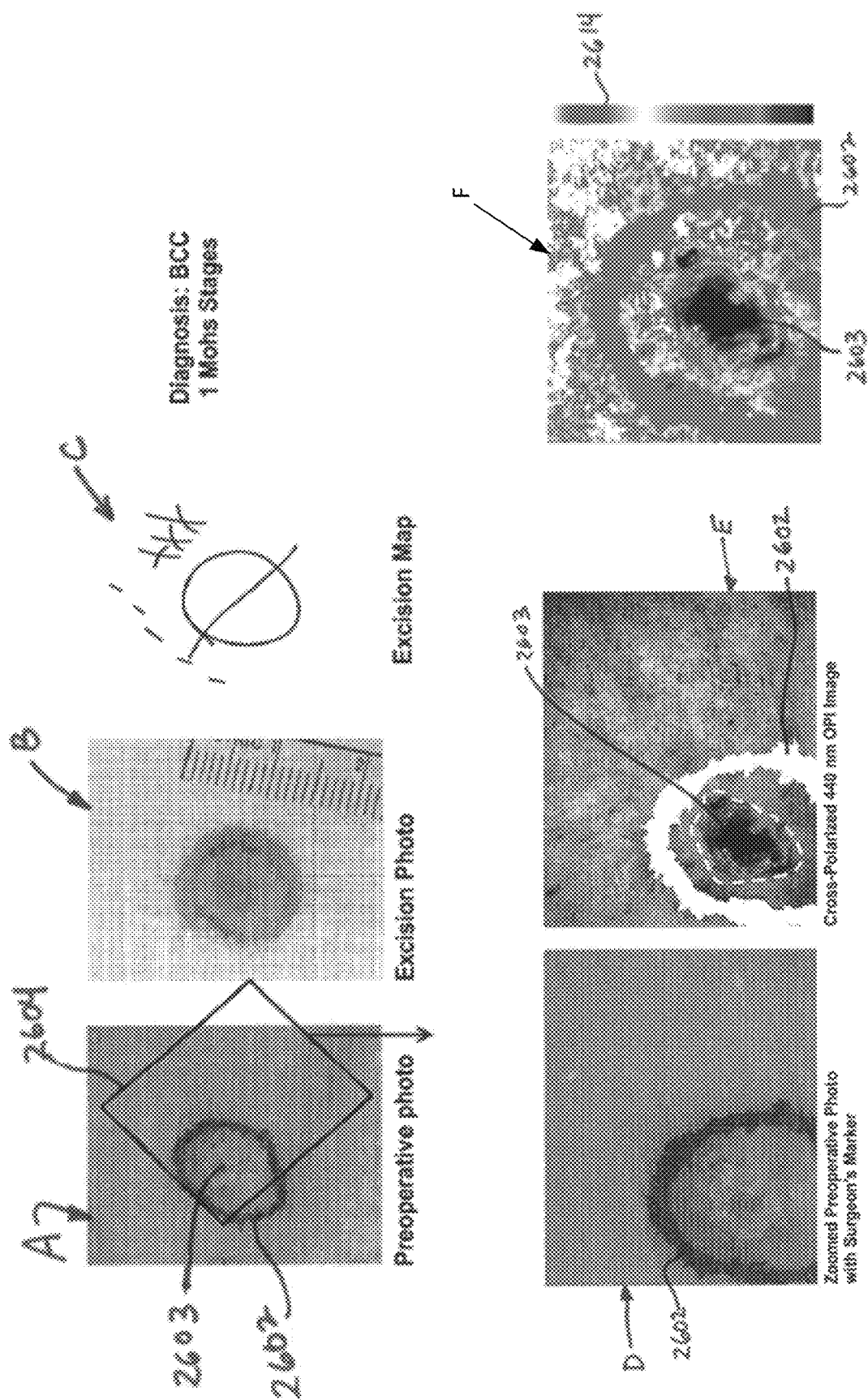
FIG. 26 is also a series of images illustrating a process for improving the surgeon marker of a tumor in accordance with the subject technology.

Referring now to FIG. 26, a series of images A-F that illustrate a margin selected by the surgeon with the surgeon marker could have been more efficiently determined using the subject technology. Image A of FIG. 26 is a preoperative photograph with a dotted margin line/surgeon marker 2602 drawn in by the surgeon around a tumor 2603. Area 2604 of the preoperative photograph is zoomed in on and shown in more detail in image D. Even with zooming in image D, again, it is difficult to determine an optimum margin line visually. Thus, when relying upon the visual surgeon marker 2602, the surgeon has a poor guide during the procedure. In fact, surgery was performed using the surgeon marker 2602 so that image B shows the incised tissue. Image C is an intraoperative Mohs map illustrating a negative margin upon analysis of the excised tissue.

Referring now to image E of FIG. 26, a cross-polarized image taken with illumination at 440 nm is shown. The field of view is 2 cm×1.5 cm. The original margin line 2602 is shown in white running excessively around the tumor, which shows as a darker area 2603. The original margin line 2602 was acquired at 640 nm and superimposed on image E. As can be seen, an improved margin line could have been drawn more closely around the tumor as a guide if the image E had been utilized in vivo before excision. As a result, more healthy tissue could have been undisturbed.

Referring now to image F of FIG. 26, a preoperative 40 nm cross-polarized image with a field of view is 1.5 cm×1 cm is shown. A boundary line identifies the surgeon marker 2602. A contrast bar 2614 is shown at the right side of image F with light contrast regions corresponding to normal tissue. Dark contrast regions correspond to areas of maximal breakdown of the collagen, and hence the presumptive area of tumor involvement. As can be seen, the surgeon marker 2602 could have been more closely drawn to the tumor to reduce the overall patient trauma. Thus again, the subject technology provides the surgeon with guidance as to how to draw an effective surgeon marker.

In view of the above examples, it is beneficial to measure the collagen structure around tumors in cross-polarized images to improve the accuracy of the surgeon's marker.

In one embodiment, the cross-polarized images of collagen structures are acquired from the skin with intact epidermis and analyzed in the following way. A xenon arc lamp combined with five narrow bandpass filters (full width at half maximum 10 nm, center wavelengths of 390 nm, 410 nm, 440 nm, 570 nm and 650 nm), is used as an illuminator. Light is delivered to the skin via a fiber-optic, linearly polarizing, ring-light illuminator with power density of 0.6 mW/cm$^2$ or less. Cross-polarized images are acquired using a CCD camera coupled with an objective lens and linearly polarizing filter. For example, a schematic of such instruments 100, 200 are shown in FIGS. 1A, 1B and FIG. 2A. These instruments 100, 200 provide field of view of up to 50 mm 50 mm and lateral resolution down to 15 to 30 μm. The articulated arm 208 enables flexibility and comfortable adjustment to the subjects. The spacer 214 has a length equal to the focal length of the objective lens to help with proper focusing distance. At the end of the spacer 214, a glass plate is placed at the point of skin contact to flatten the skin surface and to lessen patient motion artefact. A calibrated reflectance reference is also attached to the glass plate to enable quantitative assessment of the images. Refractive index matching gel can be applied to skin surface to reduce refractive index mismatch between skin and glass plate and improve light coupling into the skin and back.

Detecting cross-polarized light reflected from skin allows for adjusting depth of imaging and rejecting signal from epidermal structures. Depending on the wavelength as well as the type and optical properties of skin, the depth from which images are acquired can vary between approximately 50 to 200 um. The choice of wavelength also allows the user to highlight different skin structures, such as collagen or blood.

Figure 27B:
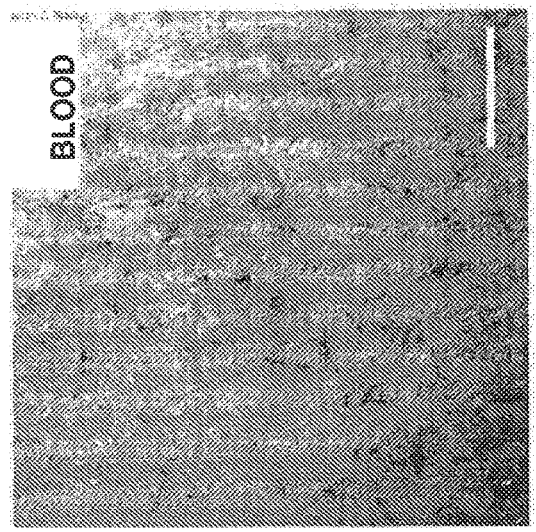
FIGS. 27A-27D show images at different wavelengths in accordance with the subject technology.
Figure 27D:
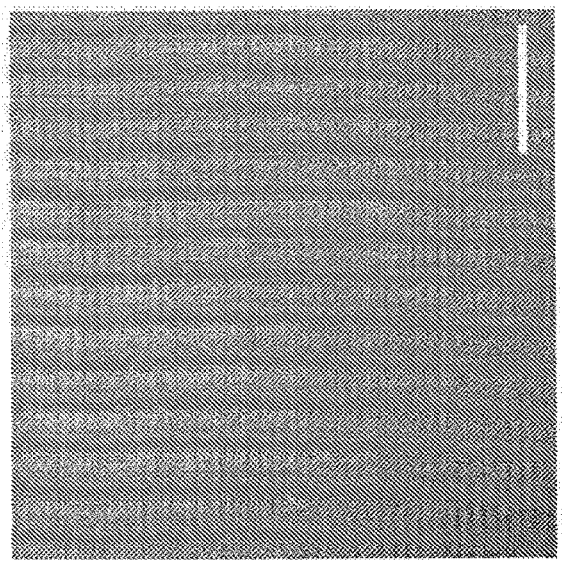
Figure 27A:
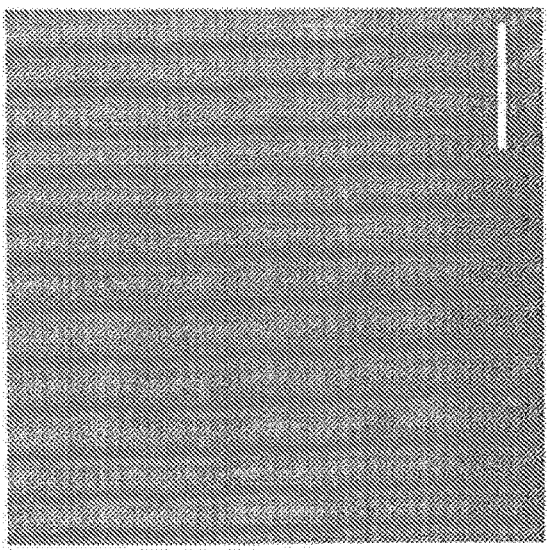
Figure 27C:
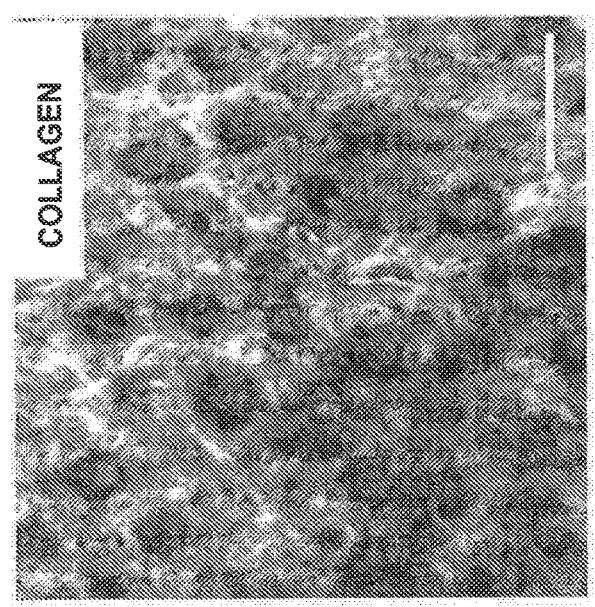

For example, FIG. 27A is an image of skin with broadband illumination. FIG. 27B is a cross-polarized image illustrating blood. FIG. 27C is a cross-polarized image illustrating collagen. Still referring to FIGS. 27A-D, after acquisition, the images are filtered using low pass and sharpen filters to reduce the noise and impact of scattering from the lower skin layers (such as lower blood plexus and subcutaneous fat) on the quality of the collagen images. Cross-polarized images at different wavelengths are shown at 440 nm, 570 nm and 690 nm in FIGS. 27B, 27C and 27D, respectively, with FIG. 27A showing a photograph of the skin with broadband illumination.

Figure 28:
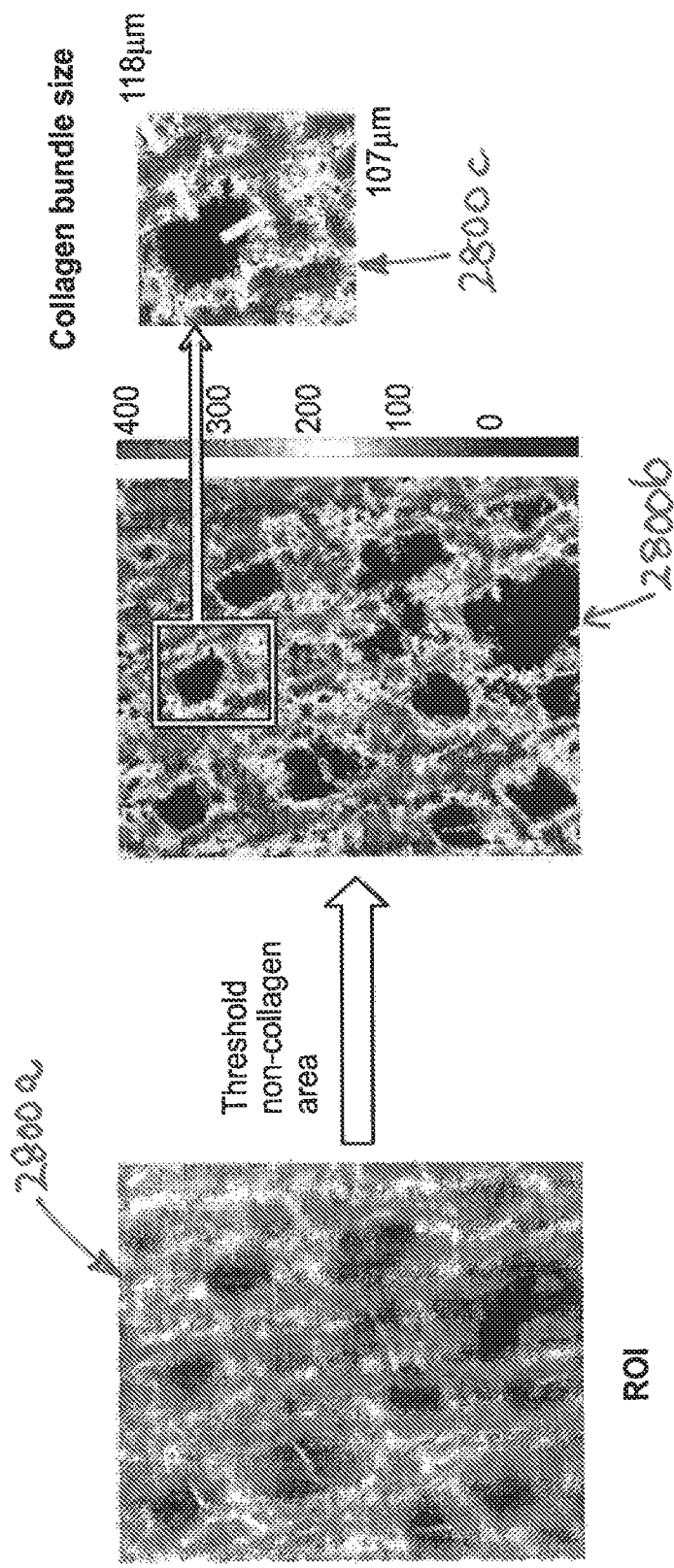
FIG. 28 shows a series of images illustrating thresh-holding the images and measuring collagen bundle size in accordance with the subject disclosure.

Referring to FIG. 28, a series of images used to evaluate the dermal structure of tissue is shown. Image 2800a was taken using 440 nm illumination as described above. The image 2800a illustrates a normal collagen structure in terms of density, size and volume. Image 2800b is a thresholded version of the image 2800a so that contrast is enhanced. Once the threshold image 2800b was obtained, sub-areas like image 2800c were studied in greater detail to confirm that the measurements of the collagen, such as collagen bundle size, measured accurately to known sizes acquired by other traditional methods. As can be seen by the 107 and 118 um measurements for collagen bundles, the subject technology can accurately measure and display the collage structure.

FIGS. 29A-C and 30A-C show example images of normal tissue from two subjects, a 24-year old and a 43-year old, respectively, to contrast age-related changes to the collagen structure. FIGS. 29A and 30A are digital pictures 2900a, 3000a. FIGS. 29B and 30B are the entire field of view collagen image 2900b, 3000b with four regions of interest highlighted. In FIGS. 29C and 30C, the four regions of interest are presented for each subject.

To compare the 24-year old and 43-year old subjects, the images are normalized using a calibrated reflectance reference. Histograms of the normalized ROI images were calculated, graphed and the full width at half maximum (FWHM) values are determined using the following formula:

$$f(x) = \frac{1}{\sigma\sqrt{2\pi}} \exp\left[-\frac{(x-x_o)^2}{2\sigma^2}\right]$$

$$FWHM = 2\sqrt{2 \ln 2}\, \sigma \approx 2.3548200\sigma$$

wherein $\sigma$ is one standard deviation and x is pixel brightness level.

An example of a normalized ROI image is the image 2800a of FIG. 28. The normalized ROI image is thresholded to about 35% to 40% brightness of which image 2800b of FIG. 28 is an example. The threshold values of the thresholded image 2800b is recorded and used to define percentage collagen area in the following manner:

% Collagen Area=(1−Threshold Value)×100%

With a plurality of subjects, parameters obtained from different ROIs can be averaged over the plurality of subjects. After summarizing the data for a statistically significant number of subjects, the results demonstrated large variance for subjects of different ages (exemplified by FIGS. 29-30). As shown in FIGS. 29C and 30C, the collagen area, representing collagen density and content, decreases with age, whereas the FWHM value, which measures the compactness of collagen bundles, increases with age. Once the in vivo collagen images are acquired and pre-processed, the resulting information could be used by a cancer surgeon, for instance, to identify the presence and lateral extension of a collagen-altering tumor, as discussed above. Additionally, the normalized reflectance information can be used by the instrument to determine a margin or surgeon marker.

To aid the surgeon, various computed features of the observed structures can be assessed, including (but not limited to): a) quantified parameters of the pixel intensity distribution, such as FWHM; b) collagen-occupied area defined as a percentage of pixels above certain threshold brightness; and c) a quantitative measure of the degree of order in the image, such as approximate entropy or Tsallis entropy.

Referring now to FIG. 31, a graphical grid 3100 of an area of tissue as analyzed using an instrument according to the subject technology is shown. The grid 3100 is divided into a number (e.g., 64) of sub-areas 3102. For example, the grid 3100 is divided into an 8×8 grid. The quantification of the selected feature parameters is conducted independently for each sub-area 3102. Then, each sub-area 3102 is then classified as one of: "lesion," "normal," or "borderline". The lesion sub-areas 3012 are noted so with a slash mark. The normal sub-areas 3012 are noted so by being left blank. The borderline sub-areas 3012 are noted so by being fully cross-hatched. A solid line 3104 approximates the actual lesion tissue boundary.

The sequence of edges separating "borderline" and "normal" sub-areas is then accepted as an estimate for the outer margin of the lesion, which is represented by a wavy line 3106. The estimates of the outer margin from consecutive images are stitched together to form an estimate for the complete lesion margin. In a preferred embodiment, prior to assessing the presence and dimensions of the lesion(s), reference images from neighboring intact skin is obtained, thus providing baseline "normal" values for the selected feature parameter(s), similar to the series of images discussed above with respect to FIGS. 29 and 30. These baseline values are then used to normalize the feature parameters of the areas under investigation and thus increase accuracy of the classification.

Several modes of using the instrument and method are available. First, a "diagnostic" mode may be used when the technique is used for initial assessment of the number and extent of the lesions during preliminary evaluation. Additionally, a "delineating" mode may be used when the technique is used intra-operatively during Mohs micrographic surgery to assess remaining lesion margins. In the delineating mode, the imaging technique can be combined with an automated surgery instrument (preferably, using directed-energy approach, such as an ablative laser). The automated surgery system can complete removal of the area delineated with the imaging technique. In the embodiment employing an ablative laser, the laser can be optically coupled onto the field of view wherein selected pixels can be illuminated at power levels sufficient to remove tissue to a selected depth.

The computer and controller of the instrument is programmed to ablate pixels within the margin defined by the boundary established using the imaging techniques described herein (e.g., along wavy line 3106 of FIG. 31). The instrument is calibrated to the image 3100. For example, the instrument can identify a virtual boundary that is used to properly orient the ablation laser beam relative to the surface topography of the tumor region. A scanning element such as a scanning mirror can be used to scan the beam in a raster mode across the tissue being ablated. A plurality of layers can be removed in sequence until the tumor is removed. A gas flow over the region can be used to remove debris during the procedure to maintain a clear field of view for imaging. The shape of the wound margins can be selected to assist in proper closure of the wound to minimize scarring. This imaging technique can also be used to record the condition of the treated region periodically after surgery to monitor whether any further treatment of the site is needed and can identify a recurrence of abnormal tissue that may indicate the potential for tumor regrowth.

In view of the above, it can be seen that the subject technology allows a clinician to identify skin lesions and characterize their lateral dimensions in an objective manner based on fundamental, inherent features of the collagen-based dermal structure of skin. The collagen structure varies between normal and cancerous skin. It is noteworthy in that the subject technology does not require use of any exogenous contrast agents. The subject disclosure significantly improves on the prior art by allowing: 1) Increased objective accuracy of detecting and delineating cancerous lesions; 2) full lesion removal as a result of surgery; 3) reduction in the number of stages in Mohs micrographic surgery, thus reducing cost and procedure time; 4) Minimization of the volume of intact healthy tissue removed during surgery, thus decreasing the time and improving aesthetic outcome; 5) Much larger field of view than currently available images devices; and 6) More rapid, real-time image acquisition which will not delay surgery.

In other words, optical polarization imaging (OPI) is a non-invasive and rapid imaging modality that highlights the structure of dermal collagen. When OPI is used preoperatively with wavelengths of 440 nm and 640 nm to perform imaging of NMSCs, OPI can provide critical guidance for surgeons about to utilize Mohs micrographic surgery (MMS) for biopsy-proven basal cell carcinomas and the like. OPI allows efficient surgical planning by identifying tumor extension beyond visibly involved skin, thus reducing the necessity for additional surgeries and the potential for recurrence.

The subject technology is an in vivo nonintrusive collagen-imaging method to diagnose skin diseases before any clinical intrusive analysis, such as a skin biopsy. Many cosmetic procedures and medication purportedly alter collagen to improve appearance or "youthfulness." Image analysis in accordance with the subject technology can therefore be developed to quantitatively define the state of patient's collagen structure, both before and after a cosmetic intervention, for instance the use of Fraxel laser or topical retinoic acid treatment. In general, the subject technology replaces the need for skin biopsy to analyze and evaluate collagen content and structure.

While the present invention has been described here in conjunction with certain preferred embodiments, a person with ordinary skill in the art, after reading the foregoing specification, can effect changes, substitutions of equivalents and other alterations to the instruments and methods described herein. Each embodiment described above can also have included or incorporated therewith such variation as disclosed in regard to any and all of the other embodiments. Thus, it is intended that the scope of the claims granted herewith be limited in breadth only by definition as defined in the specification and appended claims and any equivalents thereof.

What is claimed is:

1. An instrument for imaging a region of tissue to optimize in vivo determination of a boundary of a tumor, the instrument comprising:
    an illuminator configured for illuminating the region with at least one wavelength of light;
    an imaging detector configured for generating images of the region based upon cross-polarized light reflected from the region, wherein the at least one wavelength determines a depth of the images in the tissue; and
    a computer connected to the imaging detector and configured for receiving and storing the images, wherein the depth of the images in the tissue is selected to illustrate a collagen structure of the tissue so that the images are presented to a surgeon for determining surgical margins around the tumor based upon disruption in the collagen structure, wherein the computer is operative to:
        form a number of sub-areas of the images;
        classify each sub-area as one of: lesion; normal; and borderline based upon a reflectance of the sub-area, wherein: sub-areas classified as borderline have a reflectance within a range; sub-areas classified as normal have a reflectance above the range; and sub-areas classified as lesion have a reflectance below the range; and
        form an outer margin from stitching together consecutive borderline sub-areas.

2. The instrument of claim 1, wherein the at least one wavelength is adjusted to match a depth of the collagen structure according to a location of the region on a patient.

3. The instrument of claim 1, wherein the at least one wavelength is in a range of 380 nm to 550 nm.

4. The instrument of claim 1, further comprising a treatment device coupled to the computer for removing a portion of the region according to the surgical margins.

5. The instrument of claim 1, wherein presence of basal cell carcinoma causes the disruption of the collagen structure which results in a localized darkening in the images.

6. The instrument of claim 1, wherein the images are taken in vivo with an initial surgeon's marker drawn on the tissue.

7. The instrument of claim 1, wherein the light is monochromatic blue light.

8. The instrument of claim 1, wherein the boundary delineating the tumor based on analysis of the images is superimposed upon at least one of the images.

9. The instrument of claim 1, wherein the computer determines the surgical margins by:
    comparing a reflectance value of each of the images to a normal reflectance value, wherein: when the reflectance value of the images is below the normal reflectance value by a predetermined amount, an area associated with the respective image is identified as an unhealthy area; and when the reflectance value of the images is within the predetermined amount of the normal reflectance value, an area associated with the respective image is identified as a healthy area; and
    forming the surgical margins based upon transitions from the unhealthy areas to the healthy areas.

10. The instrument of claim 9, wherein the reflectance value is based upon factors selected from the group consisting of: an age of a patient on which the region is located; a location of the region; quantified parameters of pixel intensity distribution; collagen-occupied area defined as a percentage of pixels above a certain threshold brightness; and a quantitative measure of a degree of order in the image, such as approximate entropy or Tsallis entropy; and combinations thereof.

11. The instrument of claim 1, wherein the computer is operative to: collect normal images from a healthy region of tissue; and determine a normal reflectance value based upon the normal images.

12. The instrument of claim 1, wherein the computer is operative to apply thresholding to the images for increased contrast.

13. An instrument for imaging a region of tissue to evaluate collagen structure, the instrument comprising:
  an illumination ring configured for illuminating the region with at least one wavelength of light;
  an imaging detector configured for generating images of the region based upon cross-polarized light reflected from the region over a period of time; and
  a computer connected to the imaging detector and configured for receiving and storing the images, wherein the images are of a depth in the tissue that illustrates the collagen structure so that the images are compared over the period of time to evaluate a treatment of the region, wherein the computer is operative to:
    form a number of sub-areas of the images;
    classify each sub-area as one of: lesion; normal; and borderline based upon a reflectance of the sub-area, wherein: sub-areas classified as borderline have a reflectance within a range; sub-areas classified as normal have a reflectance above the range; and sub-areas classified as lesion have a reflectance below the range; and
    form an outer margin from stitching together consecutive borderline sub-areas.

14. A method of imaging a region of tissue to optimize in vivo determination of a boundary of a tumor, the method comprising:
  illuminating the region with at least one wavelength of light;
  generating images of the region based upon cross-polarized light reflected from the region, wherein the at least one wavelength determines a depth of the images in the tissue; and
  receiving and storing the generated images, wherein the depth of the images in the tissue is selected to illustrate a collagen structure of the tissue;
  determining a surgical margin around the tumor based upon disruption in the collagen structure, wherein determining the surgical margin includes:
    forming a number of sub-areas of the images;
    classifying each sub-area as one of: lesion; normal; and borderline based upon a reflectance of the sub-area, wherein: sub-areas classified as borderline have a reflectance within a range; sub-areas classified as normal have a reflectance above the range; and sub-areas classified as lesion have a reflectance below the range; and
    forming an outer margin from stitching together consecutive borderline sub-areas.

15. The method of claim 14, further comprising adjusting the at least one wavelength to match a depth of the collagen structure according to a location of the region on a patient.

16. The method of claim 14, wherein the at least one wavelength is in a range of 380 nm to 550 nm.

17. The method of claim 14, further comprising removing a portion of the region according to the surgical margin.

18. The method of claim 14, wherein presence of basal cell carcinoma causes the disruption of the collagen structure which results in a localized darkening in the images.

19. The method of claim 14, wherein the images are taken in vivo with an initial surgeon's marker drawn on the tissue.

20. The method of claim 14, wherein the light is monochromatic blue light.

21. The method of claim 14, further comprising superimposing the boundary delineating the tumor based on analysis of the images upon at least one of the images.

22. The method of claim 14, wherein determining the surgical margin includes:
  comparing a reflectance value of each of the images to a normal reflectance value, wherein: when the reflectance value of the images is below the normal reflectance value by a predetermined amount, an area associated with the respective image is identified as an unhealthy area; and when the reflectance value of the images is within the predetermined amount of the normal reflectance value, an area associated with the respective image is identified as a healthy area; and
  forming the surgical margins based upon transitions from the unhealthy areas to the healthy areas.

23. The method of claim 22, wherein the reflectance value is based upon factors selected from the group consisting of: an age of a patient on which the region is located; a location of the region; quantified parameters of pixel intensity distribution; collagen-occupied area defined as a percentage of pixels above a certain threshold brightness; and a quantitative measure of a degree of order in the image, such as approximate entropy or Tsallis entropy; and combinations thereof.

24. The method of claim 14, further comprising:
  collecting normal images from a healthy region of tissue; and
  determining a normal reflectance value based upon the normal images.

25. The method of claim 14, further comprising applying thresholding to the images for increased contrast.

* * * * *